US006143952A

United States Patent [19]
Srienc et al.

[11] Patent Number: 6,143,952
[45] Date of Patent: Nov. 7, 2000

[54] **MODIFIED *PSEUDOMONAS OLEOVORANS* PHAC1 NUCLEIC ACIDS ENCODING BISPECIFIC POLYHYDROXYALKANOATE POLYMERASE**

[75] Inventors: Friedrich Srienc, Lake Elmo; John K. Jackson, Plymouth; David A. Somers, Roseville, all of Minn.

[73] Assignee: Regents of the University of Minnesota, Minneapolis, Minn.

[21] Appl. No.: 09/052,689

[22] Filed: Mar. 31, 1998

[51] Int. Cl.$^7$ .............. A01H 5/00; C12N 1/21; C12N 15/31; C12N 15/52; C12N 15/70; C12N 15/81; C12N 15/82

[52] U.S. Cl. .......... 800/298; 435/69.1; 435/252.3; 435/254.2; 435/320.1; 435/440; 435/468; 435/471; 536/23.2; 536/23.7; 800/278

[58] Field of Search .............. 536/23.2, 23.7; 435/69.1, 320.1, 440, 419, 243, 252.3, 254.2, 468, 471; 800/278, 298

[56] References Cited

U.S. PATENT DOCUMENTS

| | | | |
|---|---|---|---|
| 5,229,279 | 7/1993 | Peoples et al. | 435/135 |
| 5,245,023 | 9/1993 | Peoples et al. | 536/27 |
| 5,250,430 | 10/1993 | Peoples et al. | 435/232 |
| 5,371,002 | 12/1994 | Dennis et al. | 435/142 |
| 5,395,919 | 3/1995 | Lee et al. | 528/361 |
| 5,480,794 | 1/1996 | Peoples et al. | 435/232 |
| 5,512,456 | 4/1996 | Dennis | 435/69.1 |
| 5,512,669 | 4/1996 | Peoples et al. | 536/23.2 |
| 5,518,907 | 5/1996 | Dennis | 435/141 |
| 5,534,432 | 7/1996 | Peoples et al. | 435/69.1 |
| 5,602,321 | 2/1997 | John | 435/69.1 |
| 5,610,041 | 3/1997 | Somerville et al. | 435/135 |
| 5,650,555 | 7/1997 | Somerville et al. | 800/205 |
| 5,661,026 | 8/1997 | Peoples et al. | 435/252.3 |
| 5,663,063 | 9/1997 | Peoples et al. | 435/135 |

FOREIGN PATENT DOCUMENTS

| | | |
|---|---|---|
| 8187085 | 7/1996 | Japan . |
| WO 89/00202 | 1/1989 | WIPO . |
| WO 91/00917 | 1/1991 | WIPO . |

OTHER PUBLICATIONS

Harayama S. "Artificial evolution by DNA shuffling." TIB Tech 16: 76–81, Feb. 1998.

Beevers, "Microbodies in Higher Plants," *Annual Review of Plant Physiology*, 30, 159–193 (1979).

Brandl et al., "Plastics from Bacteria and for Bacteria: Poly(β–Hydroxy–alkanoates) as Natural, Biocompatible, and Biodegradable Polyesters," *Adv. Biochem. Eng. Biotechnol.*, 41, 77–93 (1990).

Brandl et al., "*Pseudomonas oleovorans* as a Source of Poly(β–Hydroxyalkanoates) for Potential Applications as Biodegradable Polyesters," *Appl. Environ. Microbiol.*, 54, 1977–1982 (1988).

DiRusso, "Primary Sequence of the *Escherichia coli* fadBA Operson, Encoding the Fatty Acid–Oxidizing Multienzyme Complex, Indicates a High Degree of Homology to Eucaryotic Enzymes," *J. Bacteriol.*, 172, 6459–6468 (1990).

Eggink et al., "Synthesis of Poly–3–Hydroxy–Alkanoates (PHAs) by Pseudomonas: Substrates Polymerases, Bioreactor Configurations, and Products," *Abstract Pap. Am. Chem. Soc.*, 204 Meeting, Part 2, PMSE73 (1992).

Eschenlauer et al., "Production of a Heteropolymeric Polydroxyalkanoate in *Escherichia coli* from a single carbon source," *Int. J. Biol. Macromol.*, 19, 121–130 (1996).

Fromm et al., "Expression of genes transferred into monocot and dicot plant cells by electroporation," *Proc. Natl. Acad. Sci., USA*, 82, 5824–5828 (1985).

Fromm et al., "Stable Transformation of Maize After Gene Transfer by Electroporation," *Nature*, 319, 791–793 (1986).

Gagnon et al., "Crystallization Behavior and Its Influence on the Mechanical Properties of a Thermoplastic Elastomer Produced by *Pseudomonas oleovorans*," *Macromolecules*, 25, 3723–3728 (1992).

Hahn et al., "Growth Kinetics, Nutrient Uptake, and Expression of the *Alcaligenes eutrophus* Poly(β–hydroxybutyrate) Synthesis Pathway in Transgenic Maize Cell Suspension Cultures," *Biotechnol. Prog.*, 13, 347–354 (1997).

Hahn et al., "Peroxisomal Localization of PHA Synthesis in Eukaryotic Cells," *International Symposium on Bacterial Polydydroxyalkanoates '96*, (abstract and poster) 16 pgs. (1996).

Haywood et al., "Characterization of Two 3–ketothiolases Possessing Differing Substrate Specificities in the Polyhydroxyalkanoate Synthesizing Organism *Alcaligenes eutrophus*," *FEMS Microbiology Letters*, 52, 91–96 (1989).

Haywood et al., "The importance of PHB–synthase substrate specificity in polyhydroxyalkanoate synthesis by *Alcaligenes eutrophus*," *FEMS Microbiology Letters*, 57, 1–6 (1989).

Hernlern et al., "Intracellular PH in Single *Sacchromyres cerevisiae* Cells," *Biotechnol. Techn.*, 3, 79–84 (1989).

Huang, "Metabolism in Plant Peroxisomes," *Recent Advances in Phytochemistry*, 16, Ed. Creasey et al., 85–123 (1982).

Huisman et al., "Metabolism of poly(3–hydroxyalkanoates) (PHAs) by *Pseudomonas oleovorans*," *The Journal of Biological Chemistry*, 266, 2191–2198 (1991).

(List continued on next page.)

*Primary Examiner*—Amy J. Nelson
*Attorney, Agent, or Firm*—Mueting, Raasch & Gebhardt, P.A.

[57] ABSTRACT

A genetically engineered *Pseudomonas oleovorans* phaC1 polyhydroxyalkanoate (PHA) polymerase having tailored substrate specificity is provided. The modified PHA polymerase is preferably a "bispecific" PHA polymerase capable of copolymerizing a short chain length monomer and a medium chain length monomer is provided. Methods for making the modified PHA polymerase and for making nucleic acids encoding the modified PHA polymerase are also disclosed, as are methods of producing PHA using the modified PHA polymerase. The invention further includes methods to assay for altered substrate specificity.

24 Claims, 9 Drawing Sheets

OTHER PUBLICATIONS

Jackson et al., "Extending the Range of PHA Polymerase Substrate Specificity," (Poster), AIChE Annual Meeting, Session 232 (Nov. 17, 1997, (abstract available no earlier than Mar. 31, 1997)).

Kato et al., "Production of a novel copolyster of 3–hydroxybutyric acid and medium–chain–length 3–hydroxyalkanoic acids by Pseudomonas sp. 61–3 from sugars," *Appl. Microbiol. Biotech.*, 45(3), 363–370 (1996).

Kim, "Preparations, Characterization, and Modification of Poly–beta–hydrozyalkanoates from *Pseudomonas oleovorans*," Ph.D. Thesis, University of Massachusetts, Amherst (1991).

Kim et al., "Poly(β–hydroxyalkanoate) Copolymers Containing Brominated Repeating Units Produced by *Pseudomonas oleovorans*," *Macromolecules*, 25, 1852–1857 (1992).

Kindl, "Fatty Acid Degradation in Plant Peroxisomes: Function and Biosynthesis of the Enzymes Involved," *Biochemie*, 75, 225–230 (1993).

Kitamura et al., "Staining Method of Poly(3–Hydroxyalkanoic Acids) Producing Bacteria by Nile Blue," *Biotechnol. Techniq.*, 8, 345–350 (1994).

Lagaveen et al., "Formation of Polyesters by *Pseudomonas oleovorans*: Effect of Substrates on Formation and Composition of Poly–(R)–3–Hydroxyalkanoates and Poly–(R)–3–Hydroxyalkenoates," *Appl. Environ. Microbiol.*, 54, 2924–2932 (1988).

Langenbach et al., "Functional expression of the PHA synthase gene phaC1 from *Pseudomonas aeruginosa* in *Escherichia coli* results in poly(3–hydroxyalkanoate) synthesis," *FEMS Microbiol. Lett.*, 150, 303–309 (1997).

Law et al., "Assay of Poly–β–Hydroxybutyric Acid," *J. Bacteriol.*, 82, 33–36 (1961).

Lazarow et al., "Biogenesis of Peroxisomes," *Ann. Rev. Cell Biol.*, 1, 486–530 (1985).

Leaf et al., "*Saccharomyces cerevisiae* expressing bacterial polydroxy butyrate synthase produces poly–3–hydroxy butyrate," *Microbiology* (*Reading*), 142, 1169–1180 (1996).

Lee, "Bacterial Polyhydroxyalkanoates," *Biotechnol. Bioeng.*, 49, 1–14 (1996).

Lee et al., "Regulatory Effects of Cellular Nicotinamide Nucleotides and Enzyme Activities on Poly(3–Hydroxybutyrate) Synthesis in Recombinant *Escherichia coli*," *Biotechnol. Bioeng.*, 52, 707–712 (1996).

Lee et al., "Production of poly(3–hydroxybutyric acid) by recombinant *Escherichia coli* strains: genetic and fermentation studies," *Can. J. Microbiol.*, 41, (suppl. 1), 207–215 (1995).

Lenz et al., "Stereochemistry of the Ring Opening Polymerization of [S]–β–Butyrolactone," *Polymer Preprints*, 31, 408–409 (1990).

Lorimer et al., "Random recombination of antibody single chain Fv sequences after fragmentation with Dnase1 in the presence of $Mn^{2+}$," *Nuc. Acids Res.*, 23, 3067–3068 (1995).

Marchessault, "Tender Morsels for Bacteria," *Trip*, 4, 163–168 (1996).

Ostle et al., "Nile Blue A as a Fluorescent Stain for Poly–β–Hydroxybutyrate," *Appl. Environ. Microbiol.*, 44, 238–241 (1982).

Peoples et al., "Poly–β–hydroxybutyrate (PHB) Biosynthesis in *Alcaligenes eutrophus* H16," *J. Biol. Chem.*, 264, 15298–15303 (1989).

Ramsay et al., "Effect of nitrogen limitation on long–side–chain poly–beta–hydroxyalkanoate synthesis by *Pseudomonas resinovorans*," *Appl. Environ. Microbiol.*, 58, 744–746 (1992).

Ren et al., "Substrate specificity of poly–3–hydroxyalkanoate polymerases from *Pseudomonas oleovorans* GPo1," presented in a poster at the meeting of the International Symposium on Bacterial Polyhydroxyalkanoates 1996, Davos, Switzerland, Aug. 18–23, 1996.

Rhodes et al., "Genetically Transformed Maize Plants from Protoplasts," *Science*, 240, 204–207 (1988).

Riis et al., "Gas Chromatographic Determination of Poly–β–hyddroxybutyric Acid in Microbial Biomass After Hydrochloric Acid Propanolysis," *J. of Chromat.*, 445, 285–289 (1988).

Sambrook et al., *Molecular Cloning: A Laboratory Manual*, $2^{nd}$ ed., Cold Spring Laboratory Press (1989).

Seidman et al., "High–Efficiency Transformation by Electroporation," Ausubel et al., Eds., *Short Protocols in Molecular Biology*, John Wiley & Sons, Inc., New York, Third Edition, 1.22–1.23 (1995).

Steinbüchel, "A Pseudomonas strain accumulating polyesters of 3–hydroxybutyric acid and medium–chain–length 3–hydroxyalkanoic acids," *Appl. Microbiol. Biotech.*, 37, 691–697 (1992).

Steinbüchel, "Polyhydroxyalkanoic Acids," *Biomaterials: Novel Materials from Biological Souces*, Stockton Press: New York, 123–213 (1991).

Stemmer, "DNA shuffling by random fragmentation and reassembly: In vitro recombination for molecular evolution," *Proc. Natl. Acad. Sci. USA*, 91, 10747–10751 (1994).

Tabor, "Deoxyribonuclease I(Dnase I)," Ausubel et al., Eds., *Current Protocols in Molecular Biology*, John Wiley & Sons, Inc., Sections 3.13.1–3.13.2 (1989).

Timm et al., "Formation of Polyesters Consisting of Medium–Chain–Length 3–Hydroxyalkanoic Acids from Gluconate by *Pseudomonas aeruginosa* and Other Fluorescent Pseudomonads," *Appl. Environ. Microbiol.*, 56, 3360–3367 (1990).

Tolbert, "Microbodies—Peroxisomes and Glyoxysomes," *The Biochemistry of Plants*, 1, Academic Press, Inc., 359–388 (1980).

Volokita, "The Carboxy–Terminal End of Glycolate Oxidase Directs a Foreign Protein into Tobacco Leaf Peroxisomes," *The Plant Journal*, 1, 361–366 (1991).

Wallace et al., "Plant Organellular Targeting Sequences," *Plant Molecular Biology*, Ed. Croy, BIOS Scientific Publishers Limited, 287–292 (1993).

Xiang et al., "A Modified Alkaline Lysis Miniprep Protocol Using a Single Microcentrifuge Tube," *Bio Techniques*, 17, 30–32 (1994).

Zhao et al., "Optimization of DNA shuffling for high fidelity recombination," *Nuc. Acids. Res.*, 25, 1307–1308 (1997).

If p=1:

$$PHA_{SCL} \begin{cases} R = -CH_3 & \Rightarrow P(3HB) \\ R = -CH_2CH_3 & \Rightarrow P(3HV) \end{cases}$$

$$PHA_{MCL} \begin{cases} R = -(CH_2)_2CH_3 & \Rightarrow P(3HH) \\ R = -(CH_2)_4CH_3 & \Rightarrow P(3HO) \end{cases}$$

| Strain Coded | Round |
|---|---|
| Mutant 1 | P1-02 |
| Mutant 2 | P1-03 |
| Mutant 3 | P1-04 |
| Mutant 4 | P1-05 |
| Mutant 5 | P1-09 |
| Mutant 6 | P1-08 |
| Mutant 7 | P1-11 |
| Mutant 8 | P1-12 |
| Mutant 9 | P1-10 |
| Mutant 10 | P1-13 |
| Mutant 11 | P1-14 |
| Mutant 12 | P1-15 |
| Mutant 13 | P1-17 |
| Mutant 14 | P2-02 |
| Mutant 15 | G7-02 |
| Mutant 16 | G7-07 |
| Mutant 17 | G7-09 |
| Mutant 18 | G7-10 |
| Mutant 19 | G7-11 |

FIG. 8

MODIFIED *PSEUDOMONAS OLEOVORANS* PHAC1 NUCLEIC ACIDS ENCODING BISPECIFIC POLYHYDROXYALKANOATE POLYMERASE

STATEMENT OF GOVERNMENT RIGHTS

This invention was made with government support under a grant from the Department of Energy (DOE) Grant No. DE FC 05920R 22072. The U.S. Government has certain rights in this invention.

INCORPORATION BY REFERENCE

The complete disclosure set forth in the patent application entitled "POLYHYDROXYALKANOATE SYNTHESIS IN PLANTS," Ser. No. 09/052,607, filed with the United States Patent and Trademark Office concurrently herewith, is incorporated herein. The applications are commonly owned.

BACKGROUND OF THE INVENTION

Polyhydroxyalkanoates (PHAs) are a broad class of polyesters that are formed naturally in many species of bacteria as storage materials for carbon, energy and reducing equivalents. These biological compounds have drawn significant scientific and industrial interest because of their potential to be utilized as biodegradable plastics. The properties of the plastic that may be produced vary depending on the lengths and types of monomer units present in the polymer, and whether these monomer units are identical, forming a homopolymer, or different, forming a random or block copolymer. Almost all PHAs studied to date may be categorized as either $PHA_{MCL}$ (polymers formed from medium chain length, 6–14 carbon precursors) or $PHA_{SCL}$ (polymers formed from short chain length, 3–5 carbon precursors) (S. Y. Lee, *Biotechnol. Bioeng.*, 49, 1–14 (1996); see FIG. 1). Polyhydroxybutyrate (PHB) and polyhydroxyvalerate (PHV) are examples of $PHA_{SCL}$, whereas polyhydroxyhexanoate (PHH) and polyhydroxyoctanoate (PHO) are examples of $PHA_{MCL}$. $PHA_{MCL}$ polymers and copolymers also have properties superior to pure PHB (K. D. Gagnon et al, *Macromolecules*, 25, 3723–3728 (1992)).

The type of polyhydroxyalkanoate (PHA) polymerase (also commonly referred to as PHA synthase or, occasionally, PHA synthetase) that a microorganism possesses determines whether it can synthesize $PHA_{SCL}$ or $PHA_{MCL}$, but there is little crossover between the two classes. A. Steinbüchel, "Polyhydroxyalkanoic Acids" in: Byrom, D. et al., Eds., *Biomaterials: Novel Materials from Biological Sources*, Stockton Press, New York, 263–284 (1991). Bacterial PHA polymerases accordingly fall into two categories: those that catalyze polymer formation from short chain length ($C_3$–$C_5$) monomers, known as "Class I" PHA polymerases or, alternatively, $PHA_{SCL}$ polymerases, and those that catalyze polymer formation from long chain length ($C_6$–$C_{14}$) monomers, known as "Class II" PHA polymerases or, alternatively, $PHA_{MCL}$ polymerases.

*Ralstonia eutropha* (until recently known as *Alcaligenes eutrophus*) and *Pseudomonas oleovorans* are two well-studied microorganisms that possess PHA polymerases that fall into this typical pattern. The biosynthetic pathway from *R. eutropha* is essentially limited to synthesizing polyhydroxybutyrate (PHB), a $PHA_{SCL}$ made from C4 monomers. The enzymes needed for PHB synthesis in *R. eutropha* include β-ketothiolase, acetoacetyl-CoA reductase, and a $PHA_{SCL}$ polymerase commonly referred to as a polyhydroxybutyrate (PHB) synthase. These enzymes are encoded by the genes phbA, phbB and phbC, respectively, and are clustered into a single phbCAB operon (FIG. 2). A $\sigma^{70}$-like promoter sequence precedes the transcription start site, which is 307 bp upstream of phbC. The PHB polymerase from *R. eutropha* links 3-hydroxybutyryl moieties (100% relative activity) or 3-hydroxyvaleryl moieties (7.5% relative activity) to existing polyester molecules using ester bonds. It is stereospecific for D(−) stereoisomers and does not react with L(+) stereoisomers (G. W. Haywood et al., *FEMS Microbiol. Lett.*, 57, 1–6 (1989)).

The *P. oleovorans* operon contains two polymerases genes bracketing gene encoding a depolymerase (FIG. 2). The two polymerase genes, phaC1 and phaC2, exhibit 37.8% and 39.5% identity with phbC from *R. eutropha*, respectively. Both phaC1 and phaC2 are able to complement *P. putida* PHA-negative mutant GPp104 to make PHA (G. Huisman et al., *J. Biol. Chem.*, 266, 2191–2198 (1991). Both PHA polymerases isolated from *P. oleovorans* are $PHA_{MCL}$ polymerases that form polymers from medium chain length monomers. In general, the 3-hydroxylated form of whatever medium chain monomer which is supplied as carbon source is incorporated into $PHA_{MCL}$. This includes monomers containing unsaturated, branched, aromatic, and halogenated groups. For example, PHA with as many as six different types of monomer units having 6–11 carbons were produced in *P. oleovorans* grown on C6–C10 n-alkanoic acids (H. Brandl et al., *Appl. Environ. Microbiol.*, 54, 1977–1982 (1988)). When *P. oleovorans* is grown on C6 to C12 n-alkanes and 1-alkenes, $PHA_{MCL}$ containing saturated and saturated plus unsaturated monomers is synthesized (R. G. Lagaveen et al., *Appl. Environ. Microbiol.*, 54, 2924–2932 (1988)).

The PHB polymerase of *R. eutropha* has been expressed in recombinant *P. oleovorans* in an attempt to produce a copolymer incorporating both short chain length and medium chain length monomers (A. Timm et al., *Appl. Environ. Microbiol.*, 56, 3360–3367 (1990)). The transformed strain was grown on octanoate and did accumulate a polymer comprising 3HB (3-hydroxybutyrate) and 3HO (3-hydroxyoctanoate) as main constituents and 3HH (3-hydroxyhexanoate) as a minor constituent. However, the polymer was not a true copolymer or terpolymer of a short chain length (3HB) and one or more medium chain length (3HO or 3HH) monomers; rather, it was shown to be a blend (i.e., a physical mixture) of a PHB homopolymer (i.e., a $PHA_{SCL}$ homopolymer) and a poly(3HO-co-3HH) copolymer (i.e., a $PHA_{MCL}$ copolymer).

Only a few exceptions to the observed division of substrate specificities in PHA polymerases are known. Small amounts of 3-hydroxybutyrate (a C4 monomer) have been detected in PHA consisting mostly of $PHA_{MCL}$ produced by *P. resinovorans* (B. A. Ramsay et al., *Appl. Environ. Biotech.* 58, 744–746 (1992)). $PHA_{MCL}$ polymerase from *P. aeruginosa* and other pseudomonads of rRNA homology group I have been reported to incorporate 3-hydroxyvalerate (3HV, a C5 monomer) into PHA, but only if the cells are cultivated with valeric acid as sole carbon source. A. Timm et al., *Appl. Environ. Microbiol.*, 56, 3360–3367 (1990). Indeed, all of the fluorescent pseudomonads belonging to rRNA homology group I are able to synthesize $PHA_{MCL}$ whose composition is dependent upon the length of the carbon backbone in the substrate supplied (S. Y. Lee et al., *Can. J. Microbiol.*, 41, (suppl. 1), 207–215 (1995)). Pseudomonas sp. 61-3 is reported to produce a PHB homopolymer and a P(3HB-co-3HA) copolymer when glucose is presented as a substrate under nitrogen-free conditions. The copolymer consisted of a mixture of 44 mol % C4 monomer, with the rest of the polymer distributed among C6–C12 monomers (M. Kato et al., *Appl. Microbiol. Biotech.*, 44, 1–8 (1996)). This strain seems to have two polymerases, and the one with seemingly broader specificity may operate only under nitrogen-free conditions. *P. putida* strain GP4BH1 had been shown to accumulate polyester containing 3HB and $3HA_{MCL}$ when grown on various carbon sources (Steinbüchel et al., *Appl. Microbiol. Biotech.*, 37, 691–697 (1992)). This was the first naturally occurring bacterium to be described that accumulates polyester containing 3HB and 3HO at significant levels. However, this was not a true copolymer, but instead a blend (i.e., a mixture of two homopolymers) that was probably formed because of the existence of more than one polymerase in this organism.

PHA polymerases able to reliably catalyze incorporation of a broader range of precursor lengths would be extremely useful since novel PHA copolymers with unique composition and properties could be synthesized. Actual attempts to broaden the substrate specificities of bacterial PHA polymerases have thus far been confined to manipulations of the carbon source supplied to the polymer-synthesizing microorganism. Fusion or chemical mutagenesis of *R. eutropha* PHB polymerase and *P. oleovarans* PHA polymerase followed by a selection process that involves detection of accumulation of polymer by phenotypic appearance or increased density have been suggested but not been carried out (Peoples et al., U.S. Pat. No. 5,534,432). A simple and effective method for genetically engineering an extension of substrate specificity in a bacterial PHA polymerases is needed.

SUMMARY OF THE INVENTION

The present invention provides a non-naturally occurring polyhydroxyalkanoate (PHA) polymerase. The non-naturally occurring PHA polymerase preferably comprises a naturally occurring PHA polymerase that has been altered or modified in any way, for example by way of genetic engineering, mutation, or the like, to have a non-naturally occurring substrate specificity. Preferably, the modified PHA polymerase is capable of copolymerizing a short chain length monomer carbon substrate and a medium chain length monomer carbon substrate. As such, this "bispecific" PHA polymerase represents a melding of the enzymatic activities of two known classes of PHA polymerases: one that polymerizes short chain length monomers (typified by PHB polymerase of *Ralstonia eutropha*), and another that polymerizes medium chain length monomers (typified by PHA polymerase of *Pseudomonas oleovorans*). The bispecific PHA polymerase of the invention accordingly has a substrate specificity that is broadened or extended when compared to the specificities of either of the known classes of PHA polymerases.

The invention further provides a method for making a nucleic acid fragment that contains a nucleotide sequence encoding a modified polyhydroxyalkanoate (PHA) polymerase having a non-naturally occurring substrate specificity. Preferably, the modified PHA polymerase is capable of copolymerizing first and second carbon substrates. The method includes altering the nucleotide sequence of a first nucleic acid fragment that encodes a PHA polymerase capable of polymerizing a first carbon substrate to yield a nucleotide sequence encoding a modified PHA polymerase capable of copolymerizing the first carbon substrate and a second carbon substrate. Where the first carbon substrate is a short chain length monomer (e.g., a C3–C5 monomer) and the second carbon substrate is a medium chain length monomer (e.g., a C6–C14 monomer), or vice versa, the resulting PHA polymerase is a "bispecific" PHA polymerase. A nucleic acid fragment containing a nucleotide sequence encoding a non-naturally occurring PHA polymerase, preferably a modified PHA polymerase, more preferably a bispecific PHA polymerase, is also encompassed by the present invention, along with related gene constructs, such as vectors, that contain the nucleic acid sequence encoding the non-naturally occurring PHA polymerase.

The invention further provides a method for making a non-naturally occurring PHA polymerase by expressing a nucleic acid sequence encoding the non-naturally occurring PHA polymerase. Preferably, the method involves expression, in a host cell, of the nucleotide sequence encoding the non-naturally occurring PHA polymerase such that the nucleotide sequence is transcribed and then translated to yield a functional form of the encoded protein product. The PHA polymerase made according to the present invention is a preferably modified PHA polymerase, more preferably a bispecific PHA polymerase. Optionally, the PHA polymerase of the invention can be isolated and purified from the host cell.

The invention provides a method for producing PHA using a non-naturally occurring PHA polymerase. The PHA is preferably a copolymer. In a particularly preferred embodiment, the non-naturally occurring PHA polymerase is a bispecific PHA polymerase, and the copolymer contains at least one short chain length carbon monomer and at least one medium chain length monomer. The method can comprise transforming a host cell with a nucleotide sequence encoding a bispecific PHA polymerase; expressing the bispecific PHA polymerase in the transformed host so as to make possible production in the host cell of a PHA copolymer comprising at least one C3–C5 monomer and at least one C6–C14 monomer; and isolating the PHA copolymer from the host cell. Where the host cell comprises a peroxisome, the modified PHA polymerase is preferably targeted to the peroxisome using an appropriate targeting sequence. The method can be performed in a single cell, cell culture or the like, or within a multicellular organism, such as a plant. Alternatively, the method for producing PHA can be performed in vitro. The invention is further directed to polymers, preferably copolymers, synthesized according to any of the in vivo or in vitro methods of the invention.

The invention also includes screening methods useful for identifying a bispecific PHA polymerase by detecting extensions of polymerase activity in modified PHA polymerases. Candidate transformants can be screened, and successful transformants containing bispecific PHA polymerase can be thereby identified. In one embodiment of the screening assay, enzymatic activity characteristic of a PHA polymerase that can polymerize short chain length monomers is detected by transforming a host cell with a nucleic acid fragment containing a promoter operably linked to a nucleotide sequence encoding a candidate PHA polymerase; controlling the intracellular environment of the transformed host cell to prevent formation of PHA comprising medium chain length monomers ($PHA_{MCL}$); providing in the intracellular environment a biologically active β-ketothiolase and a biologically active acetoacetyl-CoA reductase; supplying an appropriate substrate, such as glucose, to the host cell; and detecting the production of PHA. Prevention of the formation of $PHA_{MCL}$ can be achieved, for example, by selecting a host cell that does not contain at least one of the enzymes or precursors necessary for $PHA_{MCL}$ synthesis, or, as another example, by excluding selected nutrients from the culture medium so as to preclude formation of $PHA_{MCL}$. In another embodiment of the screening assay, enzymatic activity characteristic of a PHA polymerase that can polymerize medium chain length monomers is detected by transforming a host cell with a polynucleotide comprising a promoter operably linked to a nucleic acid encoding a candidate PHA polymerase; controlling the intracellular environment of the transformed host cell to prevent formation of PHA comprising short chain length monomers ($PHA_{SCL}$); supplying an appropriate substrate, such as decanoic acid, as a carbon source for the host cell; and detecting the production of PHA. Control of the intracellular environment can be achieved as described above, except that the host or culture medium is chosen or manipulated as to preclude formation of $PHA_{SCL}$, not $PHA_{MCL}$.

BRIEF DESCRIPTION OF THE DRAWINGS

FIG. 8. Key for mutant designations used in FIG. 7.

DETAILED DESCRIPTION OF THE INVENTION

Figure 1:
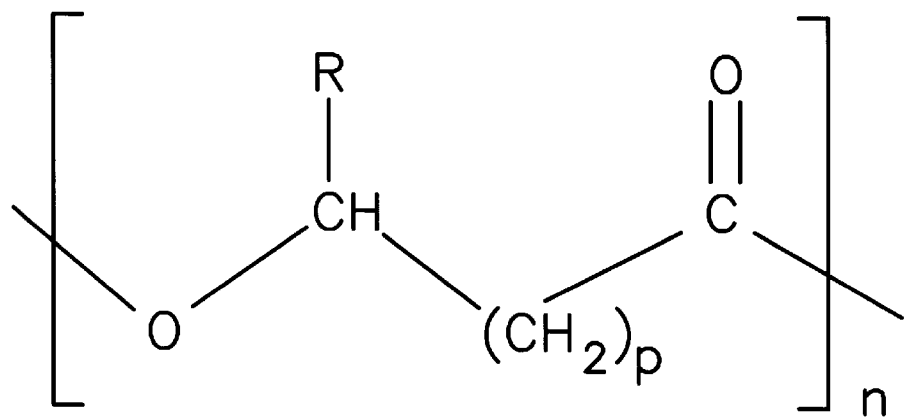
FIG. 1. General structure of polyhydroxyalkanoate, and representatives of the two distinct classes, $PHA_{SCL}$ and $PHA_{MCL}$.

Polyhydroxyalkanoates (PHAs) are polyesters of hydroxyalkanoates conforming to the general structure illustrated in FIG. 1. Each monomer contains a carboxyl and a hydroxyl functional group. Unless the R group is hydrogen, the adjacent carbon is a chiral center. The R groups and p values for several PHAs are listed in the Table below (adapted from adapted from Brandl et al., Adv. Biochem. Eng. Biotechnol., 41, 77–93 (1990); Steinbüchel, Biomaterials: Novel Materials from Biological Sources, pp. 123–213. Stockton Press: New York (1991) both of which are incorporated herein by reference, in their entireties. The value of n is typically about 100 to about 30,000.

| Selected Bacterial Polyhydroxyalkanoates. | | |
|---|---|---|
| Polyhydroxyalkanoate* | R | p |
| Poly-3-hydroxypropionate* | —H | 1 |
| Poly-3-hydroxybutyrate* | —$CH_3$ | 1 |
| Poly-3-hydroxyvalerate* | —$CH_2CH_3$ | 1 |
| Poly-3-hydroxyhexanoate (or hydroxycaproate) | —$CH_2CH_2CH_3$ | 1 |
| Poly-3-hydroxyheptanoate | —$CH_2CH_2CH_2CH_3$ | 1 |
| Poly-3-hydroxyoctanoate | —$(CH_2)_4CH_3$ | 1 |
| Poly-3-hydroxynonanoate | —$(CH_2)_5CH_3$ | 1 |
| Poly-3-hydroxydecanoate | —$(CH_2)_6CH_3$ | 1 |
| Poly-3-hydroxyundecanoate | —$(CH_2)_7CH_3$ | 1 |
| Poly-3-hydroxydodecanoate | —$(CH_2)_8CH_3$ | 1 |
| Poly-4-hydroxybutyrate* | —H | 2 |
| Poly-4-hydroxyvalerate* | —$CH_3$ | 2 |
| Poly-5-hydroxybutyrate* | —H | 3 |
| Poly-3-hydroxy-4-pentenoate* | —CH=$CH_2$ | 1 |
| Poly-3-hydroxy-2-butenoate (unsaturated chain)* | —$CH_3$ | 1 |

*These polymers are short chain length monomer polyhydroxyalkanoates, $PHA_{SCL}$.

More complex PHAs can contain olefin, branched, halogenated, phenyl, hydroxyl, cyclohexyl, ester, or nitrile R groups (R. Lenz et al., Polymer Preprints, 31, 408–409 (1990); Y. B. Kim, "Preparation, Characterization, and Modification of Poly-beta-hydroxyalkanoates from Pseudomonas Oleovorans," Ph.D. Thesis, University of Massachusetts, Amherst (1991); Y. B. Kim et al., Macromolecules, 25, 1852–1857 (1992); each of which is incorporated herein by reference, in its entirety). A list of selected constituents detected in microbial PHAs is found in Steinbuchel, Biomaterials: Novel Materials from Biological Sources, pp. 123–213, p. 128, Stockton Press: New York (1991), which is incorporated herein by reference.

Polyhydroxyalkanoates can be divided into two classes: polymers formed from short chain length carbon monomers (referred to herein as $PHA_{SCL}$) and polymers formed from medium chain length carbon monomers (referred to herein as $PHA_{MCL}$). A "short chain length carbon monomer" is a carbon monomer having 3 carbon atoms (a C3 monomer) to about 5 carbon atoms (a C5 monomer). Examples of short chain length carbon monomers include 3-hydroxybutyrate and 3-hydroxyvalerate, which are formed from glucose and glucose supplemented with propionic acid, as substrates, respectively, for the polymerase. A "medium chain length carbon monomer" is a carbon monomer having about 6 carbon atoms (a C6 monomer) to about 14 carbon atoms (a C14 monomer). Examples of medium chain length carbon monomers include straight-chain 3-hydroxyalkanoic acids with about 6 to about 12 carbon atoms, which are formed from the respective alkanoic monomer as substrate for the polymerase. In all, ninety-one PHA monomer units have been discovered to date (R. H. Marchessault, TRIP, 4, 163–168 (1996) incorporated herein by reference, in its entirety).

As used herein, the term "$PHA_{SCL}$ activity" means a polyhydroxyalkanoate polymerase activity characterized by the ability to polymerize a short chain length carbon monomer. This enzymatic activity is sometimes referred to as a "Class I" activity. A PHA polymerase having $PHA_{SCL}$ activity but not $PHA_{MCL}$ activity (described below) is referred to as a "$PHA_{SCL}$ polymerase." The polymers synthesized using a $PHA_{SCL}$ polymerase may be homopolymers or copolymers of short chain length carbon monomers. The composition of the polymer synthesized using the $PHA_{SCL}$ polymerase may be affected by the nature and identity of the particular carbon substrate or substrates provided, and/or by the growth conditions (e.g., presence or absence of nitrogen) experienced by an organism expressing the $PHA_{SCL}$ polymerase.

The term "$PHA_{MCL}$ activity" means a polyhydroxyalkanoate polymerase activity characterized by the ability to polymerize a medium chain length carbon monomer. This enzymatic activity is sometimes referred to as a "Class II" activity. A PHA polymerase having $PHA_{MCL}$ activity but not $PHA_{SCL}$ activity is referred to as a "$PHA_{MCL}$ polymerase." The polymers synthesized using a $PHA_{MCL}$ polymerase may be homopolymers or copolymers of medium chain length carbon monomers. The composition of the polymer synthesized using the $PHA_{MCL}$ polymerase may be affected by the nature and identity of the particular carbon substrate or substrates provided, and/or by the growth conditions (e.g., presence or absence of nitrogen) experienced by an organism expressing the $PHA_{MCL}$ polymerase.

A PHA polymerase having aspects of both $PHA_{SCL}$ activity and $PHA_{MCL}$ is referred to herein as a bispecific PHA polymerase. A preferred bispecific PHA polymerase is a $PHA_{SCL}$ or $PHA_{MCL}$ polymerase that has been modified to exhibit an extended or broadened substrate specificity compared to the $PHA_{SCL}$ or $PHA_{MCL}$ polymerase starting material. Polymers synthesized using a bispecific PHA polymerase include copolymers that incorporate both short chain length carbon monomers and medium chain length monomers. The composition of the copolymer synthesized using the bispecific PHA polymerase may be affected by the nature and identity of the particular carbon substrate or substrates provided, and/or by the growth conditions (e.g., presence or absence of nitrogen) experienced by an organism expressing the bispecific PHA polymerase. The extension of substrate specificity that characterizes a bispecific PHA polymerase can result from a modification of the active site of the polymerase, such that it can accommodate a wider variety of monomeric substrates. Alternatively, the extension of substrate specificity can arise from the addition of a second active site in the polymerase molecule having a different substrate specificity. It should be understood that the invention is in no way limited by the particular mechanism that causes or gives rise to the extension in substrate specificity of the PHA polymerse. A bispecific PHA polymerase may or may not be able to catalyze the synthesis of homopolymers. It may be part of a bifunctional or multifunctional enzyme or enzyme complex; for example, it may be a part of a larger fusion protein containing, for example, one or more additional enzyme involved in the PHA biosynthetic pathway. A bispecific PHA polymerase may comprise one or more sites of polymerase catalytic activity on single or multiple polypeptide chains; that is, it may have more than one catalytic domain.

The invention further includes a genetically engineered PHA polymerase having a modified substrate specificity compared to the PHA polymerase used as a starting material for genetic engineering. For example, a $PHA_{MCL}$ polymerase can be engineered according to the method of the invention so as to polymerize a different class of medium chain length monomers, thus yielding a $PHA_{MCL}$ having a polymeric composition different from that formed by the $PHA_{MCL}$ polymerase starting material.

$PHA_{SCL}$ activity and $PHA_{MCL}$ activity are typically detected by screening for the presence of polyhydroxyalkanoate (PHA) generally, without regard to the length of the monomeric constituents. These methods include visual or spectrophotometric discrimination based on colony opacity, and staining with the vital dye nile red (or nile blue) (A. G, Ostle et al., *Appl. Environ. Microbiol.*, 44, 238–241 (1982), which causes a bright yellow-red fluorescence of cells containing PHA inclusions, combined with fluorescence microscopy, fluorescence spectroscopy, or flow cytometry. Fluorescence detection of PHA may also be achieved with other lipophilic dyes. Quantification of PHA can be achieved using a flow cytometer on the basis of light-scattering properties alone. When utilized in the appropriate assays, as described below and in the following examples, PHA detected using these methods can indicate the presence of a particular one of these two enzyme activities (i.e., either $PHA_{SCL}$ activity and $PHA_{MCL}$ activity) provided the required metabolic precursors (either substrates or enzymes) for the other activity are absent. In the assays described below, extension of substrate specificity for a candidate PHA polymerase can also be indicated by comparison to a negative control comprising the non-shuffled gene, as described in more detail in the examples below.

In the assays described below, some analytic methods may be considered specific for either $PHA_{SCL}$ activity or $PHA_{MCL}$ activity because they are specific for or can distinguish homopolymers from copolymers. For example, PHB can be distinguished form copolymers containing medium chain length monomers using flow cytometry and cell sorting technology combined with nile red staining. The fluorescence emission spectrum of the copolymer exhibits a pronounced red shift compared to the fluorescence emission spectrum of the PHB homopolymer. (S. Kitamura et al., *Biotechnol. Technol.* 8, 345–350 (1994)). Thus, a population of cells containing cells expressing PHA polymerases having extended substrate specificity can be readily identified. Fluorescence ratio flow cytometry makes use of this red shift and cell sorting technology to distinguish and separate single cells having the copolymer.

Some analytic methods may be considered specific for either $PHA_{SCL}$ activity or $PHA_{MCL}$ activity because they are can be used to determine the chain length of the constituent monomers. For example, gas chromatography (GC) can be used to determine the chain length of the constituent monomers of the PHA, and thus can be used to distinguish $PHA_{SCL}$ from $PHA_{MCL}$ (Riis et al., *J. Chromatog.*, 445, 285–289 (1988)). However, because the polymer must be first hydrolyzed, GC, or GC combined with mass spectrometry (GC-MS), cannot be used to distinguish polymer from monomer. For GC and GC-MS analysis, cells containing PHA are heated in a solution of HCl and 1-propanol. This procedure lyses the cells, hydrolyzes the polymer, and forms propyl-esters from the monomer units. The propyl-esters are then extracted with 1,2-dichloroethane and analyzed with gas chromatography. Monomer peaks occur at characteristic locations, and may be resolved using GC-MS to show major functional groups (J. Hahn et al., *Biotechnol. Prog.*, 13, 347–354 (1997)).

The presence of a polymeric hydroxyalkanoate can be confirmed using nuclear magnetic resonance (NMR), for example. NMR is a very sensitive technique that can not only distinguish polymer from monomer, but can distinguish $PHA_{SCL}$ from $PHA_{MCL}$. It can also be used to distinguish heteropolymers from copolymers. For NMR analysis, PHA is extracted from the cells typically using chloroform as a solvent.

Vector constructs disclosed herein can include plasmids, viral vector, cosmids, and the like, and may be circular or linear. Vectors preferably include a promoter operably linked to the nucleotide sequence encoding the peptide or protein of interest that is to be expressed in the transgenic host. A promoter is a DNA fragment that causes transcription of genetic material. Transcription is the formation of an RNA chain in accordance with the genetic information contained in the DNA. The invention is not limited by the use of any particular promoter, and a wide variety are known. Promoters act as regulatory signals that bind RNA polymerase in a cell to initiate transcription of a downstream (3' direction) coding sequence. A promoter is "operably linked" to a nucleic acid sequence if it is does, or can be used to, control or regulate transcription of that nucleic acid sequence. The promoter used in the invention can be a constitutive or an inducible promoter. It can be tissue-specific if desired. It can be, but need not be, heterologous with respect to the host.

Vector constructs can, optionally, include a start signal for translation, such as signal ATG, at the beginning of the coding sequence of the protein to be expressed, and the correct reading frame is preferably maintained to permit expression of the nucleotide sequence to yield production of the desired protein. Vectors can also include a termination sequence, which is a regulatory sequence at the end of the coding region that is characterized by a codon for which there is no corresponding aminoacetyl-tRNA, thus ending polypeptide synthesis. A preferred termination sequence is the nopaline synthetase terminator derived from the *Agrobacterium tumefaciens* Ti plasmid (nos ter). It should be understood that vectors containing shuffled DNA, as described below, may lack either or both of a start signal and a termination sequence.

Vectors can optionally include marker sequences, typically encoding an enzyme which is generally specific to otherwise inactivate a compound in the growth medium. The inclusion of a marker sequence can render the transgenic cell resistant to an antibiotic, an herbicide, or the like, or it can confer compound specific metabolism to the transgenic cell, for example. Examples of marker sequences include those conferring resistance kanamycin, ampicillin, zeocin, phosphinothricin, and paromomycin sulfate.

The PHA polymerases of the invention that have modified or extended substrate specificity can further include an organelle-specific targeting sequence. In a preferred embodiment, the PHA polymerases are targeted to plant microbodies. Plant microbodies are spheroids of about 0.2 to about 1.5 micrometer in diameter and are bounded by a single membrane. These organelles contain a dense, often granular, protein matrix without lamelular membranes, and may contain amorphous or crystalline inclusions. Biochemically, microbodies are generally characterized by metabolic pathways associated with oxidases that produce hydrogen peroxide, and with catalase for removal of the hydrogen peroxide. In addition or alternatively, microbodies are involved with glyoxylate metabolism. See, e.g., A. Huang, "Metabolism in Plant Peroxisomes," in Recent Advances in Phytochemistry, 16, Ed. L. Creasey et al., (1982)). The metabolic pathways in microbodies are catabolic, yet the end products may be used for gluconeogenesis or other synthetic processes within the cell at other locations. See, for example, N. Tolbert, "Microbodies—Peroxisomes and Glyoxysomes," in *The Biochemistry of Plants*, Vol. 1, Academic Press, Inc. (1980), incorporated herein, by reference, in its entirety.

Historically, microbodies isolated from different tissues were given more specific names, such as peroxisomes from leaves or glyoxysomes from germinating fatty seeds. More recently, however, "microbody" has been used as a morphological term for the organelle, and "peroxisome" is the preferred biochemical term used to describe the organelle. In this nomenclature, leaf peroxisomes and glyoxysomes are classified as distinct types of peroxisomes with unique physiological functions, and may be specific for certain tissues, species, developmental stages, and environmental conditions (A. Huang, "Metabolism in Plant Peroxisomes," in Recent Advances in Phytochemistry, 16, Ed. L. Creasey et al., (1982)); Kindl, *Biochimie,* 75, 225–230 (1993)). Thus the term "peroxisome," unless specifically used in connection with a leaf peroxisome, is used herein to refer to all microbodies and includes leaf peroxisomes, glyoxysomes, "unspecialized peroxisomes" and the like. In plants, the fatty acid oxidation enzyme apparatus appears to be exclusively located within peroxisomes, including particularly glyoxysomes.

Peroxisome proteins, including integral membrane proteins, are synthesized on free polyribosomes and are imported into the organelle post-translationally (P. Lazarow et al., *Ann. Rev. Cell Biol.,* 1, 486–530 (1985)). In contrast to what is known for most other organelles, the import of peroxisomal proteins is not generally associated with any detectable modification of the imported protein, such as proteolytic removal of a pre-sequence, which indicates that the signal for targeting proteins into the peroxisome resides on the mature polypeptide. Peroxisomal targeting sequences have been found on the C-terminal of several peroxisomal proteins, and examples can be found in T. P. Wallace et al., "Plant Organellular Targeting Sequences," in *Plant Molecular Biology,* Ed. R. Croy, BIOS Scientific Publishers Limited (1993) pp. 287–288, and peroxisomal targeting in plant is shown in M. Volokita, *The Plant J.,* 3, 361–366 (1991), both of which are incorporated herein by reference, in their entireties. An exception is glyoxosomal malate dehydrogenase from watermelon, which possesses a 37 amino acid cleavable N-terminal transit peptide (T. P. Wallace et al., "Plant Organellular Targeting Sequences," in *Plant Molecular Biology,* Ed. R. Croy, BIOS Scientific Publishers Limited (1993) p. 287). Peroxisomal targeting according to the present invention can make use of any effective C-terminal or N-terminal targeting sequence, including but not limited to the ones described above, to target the heterologous genes to a peroxisome.

Targeting the modified PHA polymerase to plant microbodies is preferred because these organelles, as the site of fatty acid degradation, may provide a concentrated source of monomeric substrate for biopolymer synthesis. Paradoxically, these sites of degradative biological processes can be successfully utilized in accordance with the present invention to support the production of PHA, which is a biosynthetic process.

Optionally, expression of the nucleotide sequence encoding a modified PHA polymerase can be targeted to one or more specific plant tissues or developmental phases. Preferably, the polymerase is targeted to a seed by operably linking the nucleotide sequence encoding it to a seed-specific promoter.

The invention provides a method, preferably using recombinant DNA technology, for extending the substrate specificity of a PHA polymerase. The starting material, which is a nucleic acid fragment containing a nucleotide sequence encoding a PHA polymerase capable of polymerizing a first carbon substrate, can be either naturally occurring or non-naturally occurring. The method involves altering the nucleotide sequence of the coding region of the nucleic acid fragment to yield a nucleotide sequence encoding a modified PHA polymerase that is capable of copolymerizing the first carbon substrate and a second carbon substrate.

Preferably, the starting material is a nucleic acid fragment containing a nucleotide sequence that encodes a PHA polymerase capable of polymerizing a short chain length monomer (as the first carbon substrate), and the resulting modified PHA polymerase is one that can copolymerize the short chain length monomer and a medium chain length monomer (as the second carbon substrate), i.e., a bispecific PHA polymerase. Conversely, the starting nucleotide sequence can encode a PHA polymerase capable of polymerizing a medium chain length monomer (as the first carbon substrate), and the resulting modified PHA polymerase is one that can copolymerize the medium chain length monomer and a short chain length monomer (as the second carbon substrate), i.e., a bispecific PHA polymerase.

A bispecific PHA polymerase made in accordance with the method of the invention is a PHA polymerase that is characterized by an extended or broadened substrate specificity that includes aspects of both $PHA_{SCL}$ activity and $PHA_{MCL}$ activity. The starting material for making the bispecific PHA polymerase can be a recombinant or naturally occurring $PHA_{SCL}$ polymerase, a recombinant or naturally occurring $PHA_{MCL}$ polymerase, or a recombinant or naturally occurring bispecific PHA polymerase. In the latter case, the method of the invention yields a bispecific PHA polymerase that is even more extended or broadened than that which characterizes the PHA polymerase used as a starting material.

Alteration of the nucleotide sequence is preferably accomplished using genetic engineering techniques to produce a recombinant polynucleic acid with a nucleotide sequence that is different from the sequence of the starting material. Chemical modification of nucleic acid fragments can also be used. Any laboratory technique that can alter the nucleotide sequence by way of mutation, addition, deletion, or exchange can be employed. Suitable recombinant techniques include, but are not limited to site-directed mutagenesis, cassette mutagenesis, error-prone polymerase chain reaction and DNA shuffling. DNA shuffling (W. P. C. Stemmer, *Proc. Natl. Acad. Sci. USA*, 91, 10747–10751 (1994)), incorporated herein by reference, in its entirety) is a particularly preferred method of generating genetically altered candidate polymerases using polynucleotides comprising nucleotide sequences that encode native or recombinant PHA polymerases, or fragments thereof, as a starting material. If fragments of PHA polymerase genes are used in the DNA shuffling, the gene fragments preferably contain at least about 20 base pair, more preferably at least about 50 base pair in length. Preferably, the DNA molecule to be shuffled includes at least about 100 base pairs upstream and downstream from the translation start and stop codons, respectively, of the gene to be shuffled. DNA shuffling utilizes standard polymerase chain reaction (PCR) technology and does not require rigorous knowledge of enzyme catalytic mechanisms for success. Preferred starting materials include nucleic acids comprising phbC from *R. eutropha* (the gene that encodes a $PHA_{SCL}$), phaC1 from *P. oleovorans* (the gene that encodes a $PHA_{MCL}$), or a mixture of both genes. Nucleotide sequences for these and other suitable starting materials are readily available to one of skill in the art from protein and nucleic acid data bases such as GENBANK.

The invention provides a complementation assay for screening for $PHA_{SCL}$ activity in a PHA polymerase. The PHA polymerase to be screened is preferably a PHA polymerase that has been modified according to the present invention, as by applying DNA shuffling to the gene encoding it, in an attempt to extend its substrate specificity. The PHA polymerase to be screened is preferably capable of catalyzing the production of $PHA_{MCL}$.

The host cell used in the complementation assay for $PHA_{SCL}$ activity is preferably a bacterial or yeast cell, and does not endogenously express a $PHA_{SCL}$ polymerase; for example, *E. coli* strain DH5α (Life Technologies, Gaithersburg, Md.) is a convenient host. In order to allow complementation of the metabolic pathway for synthesis of $PHA_{SCL}$, the host cell must be engineered to express the enzymes required, other than $PHA_{SCL}$ polymerase, to cause biosynthesis of $PHA_{SCL}$. Thus, in order to assay for $PHA_{SCL}$ synthesis, the host cell should contain biologically active β-ketothiolase and a biologically active acetoacetyl-CoA reductase, preferably a reductase that yields the D-enantiomer of 3-hydroxyacyl-CoA. If either or both of these enzymes is not already present in the intracellular environment of the host cell, the host cell is transformed with genes encoding the missing enzyme(s) operably linked to a promoter. In a preferred embodiment, the $PHA_{SCL}$ complementation assay makes use of the functional PHB biosynthesis pathway from *Ralstonia eutropha* containing the constitutive promoter, β-ketothiolase, and NADPH-dependent acetoacetyl-CoA reductase from the phbCAB operon.

The host cell is also transformed with a nucleic acid fragment comprising a promoter operably linked to a nucleotide sequence, such as a gene encoding a candidate PHA polymerase. In bacterial transformations according to the present invention, typically a vector is used to transform the host cell with the desired nucleotide sequence, but in some cases DNA can be used without associated regulatory sequences. Suitable methods for transforming bacteria include electroporation or heat shock of competent cells.

Figure 3:
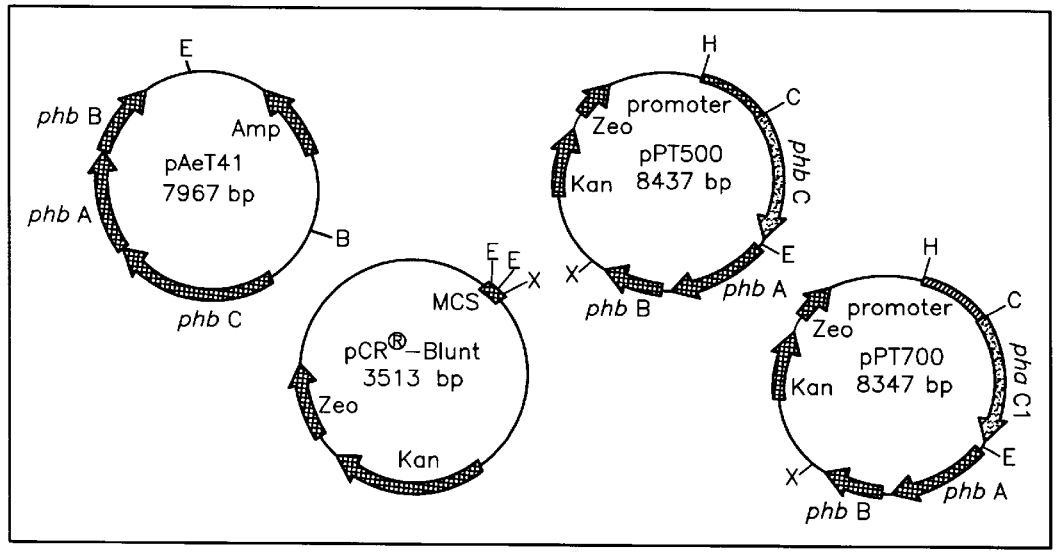
FIG. 3. Plasmid constructs. Restriction site legend: C=ClaI, E=EcoRI, H=HindIII, X=XhoI. PCR-cloning is based on pAeT41, which contains the PHB operon from R. eutropha; pPT500 is a positive control for PHB production in E. coli; pPT700 is the shuffling vector; pCR®-Blunt (Invitrogen, San Diego, Calif.) forms the backbone for both pPT500 and pPT700.
Figure 4:
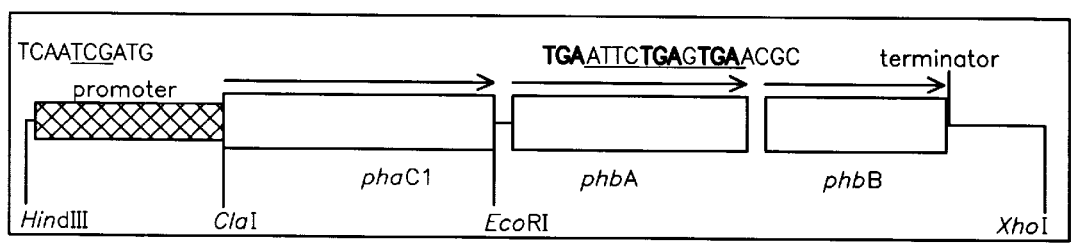
FIG. 4. pPT700 operon. Changes to native DNA are underlined. The three stop codons downstream from phaC1 are in bold type. The ClaI site is a substitution to retain ribosome binding site and RNA polymerase distances. The two extra stop codons and the EcoRI site are on a four codon insertion.

In a preferred embodiment of the $PHA_{SCL}$ complementation assay, the host cell is transformed with a single plasmid containing genes encoding β-ketothiolase, acetoacetyl-CoA reductase, and the candidate shuffled PHA polymerase, all operably linked to a single promoter. A particularly preferred plasmid is pPT700 (FIG. 3). For example, DNA shuffling can be performed using the phaC1 gene from *P. oleovorans*, which encodes a $PHA_{MCL}$ polymerase, as a starting material. The shuffled gene products (i.e., the candidate PHA polymerases) can be cloned into pPT700, then transformed into the host cell.

The $PHA_{SCL}$ assay further includes supplying the host cell with a suitable carbon source, such as glucose, that facilitates the formation of $PHA_{SCL}$, preferably PHB. The polyhydroxyalkanoate is then detected using any of the detection methods described above. Preferably, initial screening for PHA is accomplished using visual discrimination based on colony opacity, flow cytometry after staining with nile red, fluorescence spectroscopy or fluorescence microscopy. Gas chromatography, GC-MS, and NMR are more complex techniques that are preferably used for validation or confirmation of the screening results, or for further characterization of the PHA. Additionally, the cell sorting feature of the flow cytometry can be used as a selection method to identify the most promising mutants (i.e., the ones showing the highest level of $PHA_{SCL}$), which are then subjected to another round of DNA shuffling. Selection or enrichment of the transformed cell population can also be achieved by utilizing a sucrose density gradient, wherein cells containing PHA will fractionate at a different density than cells with no PHA.

In the $PHA_{SCL}$ assay, a host cell that has been successfully transformed with a $PHA_{MCL}$ having extended substrate specificity will produce PHA that contains short chain length monomers, and can be in the form of a true $PHA_{SCL}$ (i.e., a homopolymer or copolymer of exclusively C3–C5 monomers), or a copolymer of short and medium chain length monomers. Preferably, the candidate PHA polymerase exhibiting an extension of substrate specificity in the form of $PHA_{SCL}$ activity also has the ability catalyze the biosynthesis of $PHA_{MCL}$. Retention of $PHA_{MCL}$ activity is desirable because it presumably makes it more likely that the PHA polymerase will be able to catalyze the synthesis of PHA copolymers of short chain length and medium chain length monomers. In the assay for $PHA_{SCL}$ activity, only negligible amounts of $PHA_{MCL}$ are produced in the host cell even if full $PHA_{MCL}$ activity is retained by the PHA polymerase exhibiting extended substrate specificity, since the metabolic precursors for $PHA_{MCL}$ formation are not present in the host cell.

The invention also provides an assay for screening for $PHA_{MCL}$ activity in a PHA polymerase. Preferably, the PHA polymerase to be screened is a PHA polymerase that has been modified according to the present invention in an attempt to extend its substrate specificity, preferably by applying DNA shuffling to the gene encoding it. The candidate PHA polymerase to be screened is preferably capable of catalyzing the production of $PHA_{SCL}$. For example, DNA shuffling can be performed using the phbC gene from *R. eutropha*, which encodes PHB polymerase (a short chain length activity). Presence $PHA_{MCL}$ activity in the shuffled gene would evidence a broadening of the substrate specificity. Preferably, the candidate PHA polymerase retains its original $PHA_{SCL}$ activity.

In the $PHA_{MCL}$ activity assay, a host cell is transformed with a nucleotide fragment comprising a promoter operably linked to a nucleotide sequence, such as a gene encoding a candidate PHA polymerase. Typically a vector, such as a plasmid, is used to transform the host cell with the desired nucleotide fragment, as described elsewhere herein. The host cell is a bacterial cell, preferably an *E. coli* cell, that has been genetically engineered to produce the medium chain length precursors needed to accumulate significant amounts of $PHA_{MCL}$ when a gene encoding a $PHA_{MCL}$ polymerase is expressed therein. Additionally, the preferred host cells do not possess endogenous β-ketothiolase and/or acetoacetyl-CoA reductase activities sufficient to provide 3-hydroxybutyryl-CoA at significant levels in the cell. In a preferred embodiment, $PHA_{MCL}$ activity is assayed using a fadB mutant of *E.coli* (S. Langenbach et al., *FEMS Microbiol. Lett.*, 150, 303–309 (1997), more preferably an *E. coli* fadB mutant strain LS1298 (C. DiRusso, *J. Bacteriol.*, 172, 6459–6468 (1990)).

Because it is often convenient to screen for $PHA_{MCL}$ using a method that detects PHA but does not distinguish between $PHA_{MCL}$ or $PHA_{SCL}$, it is preferable to prevent production of $PHA_{SCL}$ in the transformed host cell during the $PHA_{MCL}$ assay. This is done by excluding or inactivating a biosynthetic pathway for the formation of $PHA_{SCL}$. β-ketothiolase and NADPH-dependent acetoacetyl-CoA reductase are enzymes required in addition to $PHA_{SCL}$ polymerase to produce $PHA_{SCL}$, but are not required to produce $PHA_{MCL}$. Thus, the intracellular environment of the transformed host cell used in the $PHA_{MCL}$ assay preferably lacks β-ketothiolase or NADPH-dependent acetoacetyl-CoA reductase, or both. Control of the intracellular environment can be effected by selecting a host cell that does not express one or both of these enzymes. If the vector used to transform the host cell includes either β-ketothiolase or NADPH-dependent acetoacetyl-CoA reductase or both operably linked to one or more promoters, the promoters are preferably inducible promoters, and expression of at least one of those enzymes is not induced during the $PHA_{MCL}$ assay, so as to preclude unintended formation of $PHA_{SCL}$.

During the $PHA_{MCL}$ assay the transformed host cell is supplied with at least one carbon source capable of serving as a substrate for $PHA_{MCL}$ polymerase. Preferably, the transformed host cell is supplied with an alkanoic acid such as octanoic acid, nonanoic acid, decanoic acid, undecanoic acid, dodecanoic acid, and higher order alkanoic acids. Decanoic acid is preferred. The substrate is preferably provided in an amount sufficient to be a non-limiting reactant in the biosynthesis of $PHA_{MCL}$.

$PHA_{MCL}$ biosynthesized in the host cell is detected using any convenient method. As long as the production of $PHA_{SCL}$ is prevented, a screening method that detects PHA but does not distinguish between $PHA_{SCL}$ or $PHA_{MCL}$ can be used. Such methods include optical discrimination based on colony opacity or staining with nile red combined with fluorescence microscopy, fluorescence spectroscopy, or flow cytometry. Alternatively, detection methods specific for $PHA_{MCL}$ can be used, such as GC, GC-MS and NMR. In this case, although still preferable, it may not be necessary to control the intracellular environment of the transformed host so as to preclude production of $PHA_{SCL}$, unless prevention of $PHA_{SCL}$ production is necessary to reliably detect very small amounts of $PHA_{MCL}$ in an otherwise large background of $PHA_{SCL}$.

If it is desired to test a candidate PHA polymerase for both $PHA_{MCL}$ activity and $PHA_{SCL}$ activity, a single vector can be used to transform the host cells in both assays. The preferred vector comprises ketothiolase and acetoacetyl-CoA reductase genes, preferably phbA and phbB from *R. eutropha*, operably linked to an inducible promoter, and the candidate PHA polymerase operably linked to a different, constitutive promoter.

It will be appreciated that the candidate PHA polymerase to be assayed in either the $PHA_{MCL}$ activity assay or $PHA_{SCL}$ activity assay can be the product of using DNA shuffling to shuffle two or more PHA polymerase genes together. Preferably, at least one of the genes encodes a $PHA_{SCL}$ polymerase and at least one other encodes a $PHA_{MCL}$ polymerase.

The present invention further includes transgenic organisms that have been transformed with and express a nucleotide sequence encoding a modified, preferably a bispecific PHA polymerase. The nucleotide sequence encoding the a modified PHA polymerase can, but need not be, incorporated into the genome of the host organism. Host organisms that can be transformed with a nucleotide sequence encoding a modified PHA polymerase include prokaryotic or eukaryotic cells. Preferred eukaryotic cells are yeast cells and plant cells. PHB synthesis has been achieved in *Saccharomyces cerevisiae* cells that have been transformed with a single gene from the PHB pathway (i.e., PHB polymerase) and there is evidence that suggests that the precursors for PHB synthesis in yeast are produced from peroxisomal β-oxidation. The precursor for PHB synthesis is likely not derived from fatty acid synthesis but is likely derived through the action of the peroxisomal enzymes, making peroxisomal targeting of the enzyme particularly desirable. In the case of plant cells, the cells can be either undifferentiated or differentiated. Especially preferred as a host organism is a whole plant. In particularly preferred transgenic plants, the bispecific PHA polymerase is targeted to plant peroxisomes, more preferably to glyoxysomes. The transgenic organisms of the invention are capable of producing polyhydroxyalkanoate copolymers that contains both short chain length monomers (C3–C5) and medium chain length monomers (C6–C14).

Methods for transforming plant cells are well known. For example, plant cells, including plant tissues, can be transformed using electroporation, in which a solution of protoplasts and DNA fragments is exposed to high voltage electricity, which allows plasmids to pass through the plasma membrane (See, e.g., Fromm et al., *Proc. Natl. Acad. Sci.*, 82, 5824–5828 (1985); Fromm et al., *Nature*, 319, 791–793 (1986); and Rhodes et al., *Science*, 240, 204–207 (1988)). Another suitable method is microprojectile bombardment (also known as "biolistic") transformation, in which DNA-coated micro-projectiles are typically fired into target cells or tissues. Plants may then be regenerated from the transgenic callus cultures formed. The infusion of DNA through microprojectile bombardment is a stochastic process. There is a small chance that a given cell will receive a working copy of the gene of interest. It is therefore desirable to expose a large number of cells to the treatment to ensure that transgenic cells are produced. In addition, gene function may be lost over time as a result of the cells' genetic repair mechanisms. This may be postponed by always growing the cells in the presence of the selective agent, which will kill cells that have lost their recombinant genes and will prevent the dominance of such cells in the culture.

Another well-known technique is based upon Agrobacterium-mediated transformation wherein the (Ti) plasmids of *A. tumefaciens* are used to deliver DNA to the plant host by way of infection. Other methods include chemical stimulation of DNA uptake by protoplasts, electroinjection of intact plant cells, liposome-mediated transformation of protoplasts, and DNA transformation by direct injection into plants.

The invention further includes constituent tissues, organs, and components of the transgenic plants, for example seeds and leaves. Preferably, transgenic organisms either inherently contain, or are further genetically altered to contain, β-ketothiolase and acetoacetyl-CoA reductase to provide a functional pathway for the production of acetyl CoA monomers. Methods for transforming bacteria, plant cells and whole plants, β-ketothiolase and acetoacetyl-CoA reductase have been described. (See, e.g., Somerville et al., U.S. Pat. No. 5,650,555; Peoples et al., U.S. Pat. No. 5,245,023; Peoples et al., U.S. Pat. No. 5,534,432; Peoples et al., U.S. Pat. No. 5,250,430; Peoples et al., U.S. Pat. No. 5,663,063).

In vitro production of copolymers containing short and medium chain length monomeric constituents is also included in the present invention. A modified PHA polymerase is produced in an appropriate host cell, such as *E. coli* or yeast, isolated and purified, and used to catalyze the production of copolymer from the desired substrates. For example, a bispecific PHA polymerase of the invention can be supplied with at least one short chain length carbon substrate (e.g., propionic acid or valeric acid) and/or a carbon source that is metabolized into a short chain length carbon substrate (e.g., glucose), together with a medium chain length carbon substrate (e.g., a C5–C12 alkanoic acid) and/or a carbon source that is metabolized into a medium chain length carbon substrate in an appropriate buffer. The reaction is allowed to proceed for a time and under conditions effective to yield a PHA copolymer, which can be detected as described herein, isolated, and purified. Preferably, the in vitro synthetic reaction is conducted at about 30° C. and is allowed to proceed for up to about 2 hours.

Methods for isolating and purifying polyhydroxyalkanoate from host organisms, and for quantifying PHA, are well-known in the art. See, e.g., Law et al., *J. Bacteriol.*, 82, 33–36 (1961) for spectrophotometric quantification of PHB.

Advantages of the invention are illustrated by the following examples. However, the particular materials and amounts thereof recited in these examples, as well as other conditions and details, are to be interpreted to apply broadly in the art and should not be construed to unduly restrict or limit the invention in any way.

EXAMPLE I

Extension of Substrate Specificity of *Pseudomonas oleovorans* phaC1 Polyhydroxyalkanoate ($PHA_{MCL}$) Polymerase Summary. The presence and function of "Class I" polymerase activity ($PHA_{SCL}$ polymerase activity) in *Escherichia coli* strain DH5α may be readily detected through complementation of the PHB pathway from *R. eutropha*, according to the method described below. Colonies that produce PHB appear opaque, while colonies without a functional PHB pathway appear transparent. In this experiment, DNA shuffling was performed on the *Pseudomonas oleovorans* phaC1 polyhydroxyalkanoate (PHA) polymerase in an attempt to alter its precursor specificity. The specificity of the native polymerase is almost completely limited to medium chain length 3-hydroxyacyl-CoA precursors ($C_6$–$C_{12}$). The objective was to increase the fraction of short chain length ($C_4$–$C_5$) precursors this enzyme could incorporate into PHA. A ColE1-based vector was constructed to allow sensitive detection of PHB production by the phaC1 polymerase in *Escherichia coli*. This plasmid was based on complementation of the functional PHB biosynthesis pathway from *Ralstonia eutropha* (formerly *Alcaligenes eutrophus*), containing the constitutive promoter, β-ketothiolase, and NADPH-dependent acetoacetyl-CoA reductase from the phbCAB operon. A screen for increased PHB production was developed that included optical discrimination based on colony opacity, flow cytometry analysis after staining with nile red, and gas chromatography.

Materials. The plasmid pAeT41 (FIG. 3) was obtained from the Massachusetts Institute of Technology in (O. P. Peoples et al., *J. Biol. Chem.*, 264, 15298–15303 (1989)). This plasmid resulted from the initial cloning the PHB operon (also known as the phbCAB operon) from *R. eutropha* comprising the genes phbC, phbA and phbB, together with the promoter, into pUC18 as a BamHI/EcoRI insert. Plasmid pAeT41 was used in this study as a source of genetic material for the DNA shuffling vector pPT500 as described below. Plasmid pCR®-Blunt (Invitrogen, San Diego, Calif.; FIG. 3) formed the backbone for both pPT500 and pPT700 constructs. The gene phaC1 from *P. oleovorans* was obtained from B. Witholt of the Swiss Federal Institute of Technology.

Plasmids were routinely grown in *Escherichia coli* strain DH5α (Life Technologies™, Gaithersburg, Md.). DH5α was also used for PHB accumulation. LB medium contained 10 g tryptone, 5 g yeast extract, and 10 g NaCl per liter). 2×YT medium contained 16 g tryptone, 10 g yeast extract and 5 g NaCl per liter. Addition of 1–2% (wt/vol) glucose (Sigma Chemical Company, St. Louis, Mo.) aided production of PHB in *E. coli* (see I. Y. Lee et al., *Biotechnol. Bioeng.*, 52, 707–712 (1996), incorporated herein by reference, in its entirety). Dilution buffer consisted of 0.85% (w/v) NaCl and 0.01% (v/v) Tween 20 (Sigma Chemical Company, St. Louis, Mo.). As used herein, % wt/vol (i.e., percent weight/volume) measurements mean grams per 100 mL. For example, a 1% wt/vol solution is 1 gram solute per 100 mL solution.

Plasmids were typically isolated from *E. coli* using a rapid alkaline lysis technique (C. Xiang et al., *BioTechniques*, 17, 30–32 (1994)). All restriction enzymes, Taq DNA polymerase, and T4 DNA ligase were purchased from Life Technologies™ (Gaithersburg, Md.).

Polymerase chain reaction (PCR) conditions. Polymerase chain reaction was performed utilizing Cloned Pfu DNA polymerase (Stratagene, La Jolla, Calif.), according to the protocols of, and using the 10× reaction buffer supplied by, the manufacturer. The final reaction mix contained 0.025 U $\mu l^{-1}$ Pfu DNA polymerase, 0.2 mM each dNTP, 0.4 $\mu$M each primer, 20 mM Tris.HCl (pH 8.8), 2 mM $MgSO_4$, 10 mM KCl, 10 mM $(NH_4)_2SO_4$, 0.1% Triton X-100, and 100 $\mu$g $ml^{-1}$ nuclease-free bovine serum albumin (BSA). A typical themocycling program consisted of 95° C. for 1 minute; 95° C. for 45 seconds, 55–60° C. for 45 seconds, 72° C. for 2 minutes $kb^{-1}$ of PCR target (25 cycles); followed by 72° C. for 10 minutes.

Plasmid construction: pPT500 (FIG. 3). This plasmid was formed using PCR-cloning of various constituents of the phbCAB operon initially present on pAeT41. The promoter was amplified using the primers GGGAGATCTCCCGGG-GAAGTACCTTGCCGA (SEQ ID NO:1) and AGGATC-GATTGATTGTCTCTCTGCCGTCAC (SEQ ID NO:2) which give a BglII upstream and a ClaI downstream restriction site. PHB synthase (phbC) was amplified using the primers ATTATCGATGGCGACCGGCAAAGGCGCGGC (SEQ ID NO:3) and GCCGAATTCATGCCTTG-GCTTTGACGTATC (SEQ ID NO:4) which give a ClaI upstream and an EcoRI downstream restriction site. The downstream genes β-ketothiolase (phbA, EC 1.1.1.36) and acetoacetyl-CoA reductase (phbB, EC 2.3.1.9) were amplified as a single length of DNA using the primers CAC-GAATTCTGAGTGAACGCTTGCATGAGT-GCCGGCGTG (SEQ ID NO:5) and ATACTCGAGCCGCGAGGGCCGCGCTGCACG (SEQ ID NO:6) which give an upstream EcoRI site, include the downstream terminator region, and add two stop codons so that any gene expressed between ClaI and EcoRI is followed by stop codons in all three reading frames.

pPT500 was constructed from the amplified genetic material in a series of steps. First, the promoter PCR product described above was cloned into the Zero Blunt™ PCR Cloning Kit (pCR®-Blunt Vector) from Invitrogen (San Diego, Calif.). PHB synthase (phbC) was also captured using the same kit. The promoter was then removed by digesting with BglII/ClaI, and this fragment was inserted behind PHB synthase on the latter plasmid by digestion with BamHI/ClaI, and subsequent ligation. The phbAB PCR product was then inserted directly by digestion of both the PCR product and the plasmid that already contained the promoter and PHB synthase with EcoRI/XhoI and subsequent ligation. The resulting plasmid, pPT500, was used both as a positive control for PHB production in *E. coli*, and as a template for DNA shuffling as described below.

Plasmid construction: pPT700 (FIG. 3). pPT700 is the plasmid that was used for DNA shuffling. First, the gene phaC1 was obtained by performing polymerase chain reaction on pGeC422, a vector containing PHA polymerase genes isolated from *P. oleovorans* GPol (G. W. Huisman et al., *J. Biol. Chem.*, 266, 2191–2198 (1991)). The primers used were ATTATCGATGAGTAACAAGAACAACGAT-GAG (SEQ ID NO:7) and GGAATTCAACGCTCGT-GAACGTAGGT (SEQ ID NO:8), which give a ClaI upstream and an EcoRI downstream restriction site. pPT700 was constructed by first removing the PHB synthase gene (phbC from *R. eutropha*) from pPT500 by digestion with ClaI/EcoRI, then ligating in its place the *P. oleovorans* phaC1 PCR product, also digested with ClaI/EcoRI. The phbA and phbB genes from *R. eutropha* were left in place on pPT700, so that if DNA shuffling (described below) resulted in some level of $PHA_{SCL}$ activity for the *P. oleovorans* $PHA_{MCL}$ polymerase, the other two enzymes needed to form $PHA_{SCL}$ polymer (i.e., β-ketothiolase and acetoacetyl-CoA reductase) would be present to complete the metabolic pathway. See the results and discussion section, below.

A second pPT700-type plasmid was also made that included, as the polymerase gene to be shuffled, a PCR product containing phaC1 from *P. oleovorans* and, additionally, approximately 200 bp upstream and downstream from the gene. The primers TATCGGAATGGACG-CAAG (SEQ ID NO:9) and CATGATGACTTCGCTCACC (SEQ ID NO:10) were used to obtain that PCR product.

DNA shuffling. The starting material for DNA shuffling was either the entire pPT700 plasmid or the phaC1 gene after removal from pPT700 using a ClaI/EcoRI restriction digest. Between 1–5 $\mu$g of starting material was digested using DNase I at a concentration of 0.15–1.5 U in a 100 $\mu$l reaction (Stratagene, La Jolla, Calif.) at 37° C. for 10 minutes to 1 hour under conditions as recommended by the manufacturer. These conditions were typically 40 mM Tris.HCl pH 7.4, 6 mM $MgCl_2$, and 2 mM $CaCl_2$. The concentration of DNase I, as well as reaction time, were empirically optimized for each shuffling round by first digesting a small portion of the starting material and stopping small aliquots of the reaction at short intervals using phenol:chloroform (Amresco, Solon, Ohio).

A range of short fragments, typically 50–350 bp, were then isolated using a 2% agarose gel and collected by electroelution onto DE81 DEAE cellulose paper (Whatman, Clifton, N.J.). DEAE-cellulose is reported to be optimal for small fragments and to result in very pure DNA. Other options to isolate the DNA at this stage include dialysis tubing and Gene Clean™ (BIO 101). The latter is intended for DNA fragments longer than 500 bp which is above the desired cut-off point. These materials and techniques are described in detail in J. Sambrook et al., *Molecular Cloning: A Laboratory Manual*, Cold Spring Harbor Laboratory Press, New York (1989), which is incorporated herein in its entirety.

The short, purified fragments were placed into a primerless PCR reaction with 0.025 U $\mu l^{-1}$ Taq DNA polymerase (Life Technologies™, Gaithersburg, Md.) using the 10× reaction buffer supplied by the manufacturer. The reaction mixture (100 $\mu$l) contained 20 mM Tris.HCl (pH 8.4), 50 mM KCl, 0.2 mM each dNTP, and $MgCl_2$ added to 1–2 mM. In the primerless PCR step, the fragments were highly concentrated. The PCR program for reassembling the phaC1 gene as isolated from a ClaI/EcoRI digest of pPT700 was 94° C. for 3 minutes; 94° C. for 30 seconds, 50–55° C. for 45 seconds, 72° C. for 1 minute 45 seconds (80 cycles); followed by 72° C. for 2 minutes. For whole plasmid reassembly the PCR program used was 94° C. for 3 minutes; 94° C. for 30 seconds, 50–55° C. for 45 seconds, 72° C. for 30 seconds increasing 7 seconds each cycle (80 cycles); followed by 72° C. for 2 minutes.

After completion of primeness PCR, the mixture was diluted 25–40 times into a new 100 $\mu$l reaction, and primers were included to amplify the reassembled product in order to allow for efficient ligation back into pPT700. This PCR reaction contained the same ingredients as primerless PCR, except for addition of primers to 0.4 μM. The primers used were the same as those initially used to PCR-clone phaC1, described above. The PCR with primers themocycling program was: 94° C. for 3 minutes; 94° C. for 30 seconds, 60° C. for 45 seconds, 72° C. for 1 minute 45 seconds (40 cycles); followed by 72° C. for 2 minutes.

This PCR product was then ligated into pPT700 by digestion of the plasmid and the PCR product with ClaI/EcoRI and subsequent ligation. Electroporation with freshly grown DH5α cells (C. E. Seidman et al., "High-Efficiency Transformation by Electroporation" in: Ausubel, F. M. et al., Eds., *Short Protocols in Molecular Biology*, John Wiley & Sons, Inc., New York, Third Edition, 1.22–1.23 (1995)) was used to transfer the ligated vectors into DH5α.

Screening of the DNA-shuffled mutants: colony opacity. The transformed DH5α cells were plated onto 2× YT plates containing 1% (wt/vol) glucose and 100 μg ml$^{-1}$ kanamycin. Typically 1000 colonies resulted. These colonies were allowed to grow for 2–3 days at 37° C. Colonies that accumulate PHA appear white, whether the PHA is PHA$_{SCL}$ or PHA$_{MCL}$. Presumably, since PHA$_{MCL}$ production was not enabled in the host cell, white colonies produced PHA$_{SCL}$. Approximately 20 of the whitest colonies and 20 of the most transparent colonies were selected for further screening, based on visual discrimination.

Screening of the DNA-shuffled mutants: flow cytometry. In the next stage of the screen, each colony was inoculated into 15 ml culture tubes containing 2× YT medium with 100 μg ml$^{-1}$ kanamycin, so that the plasmids could be isolated and tested by restriction digest. This liquid culture, in which the cells had grown to saturation, was also gridded by dropping 10 μl of each liquid culture onto 2× YT+1% (w/v) glucose plates. These spots were allowed to grow for 2–3 days at 37° C. and resuspended at equal optical densities in 1 ml dilution buffer in microcentrifuge tubes. An aliquot (270 μl) of a solution that was 10 μg/ml nile red in ethanol were added and the tubes were incubated 5 minutes at room temperature. These cells were spun for 1 minute at 14,000 rpm in a microcentrifuge, and resuspended in ice-cold dilution buffer. These samples were kept on ice until they could be examined in the flow cytometer. DNA from samples that produced the greatest amount of PHB, as determined by flow cytometer analysis, were pooled together after each round of shuffling and used for the next round.

Flow cytometry was performed on a Cytofluorograph IIs (Ortho Diagnostic Systems, Inc., Westwood, Mass.) equipped with a Coherent Innova® 90-5 argon ion laser (Coherent, Palo Alto, Calif.) operated at a wavelength of 488 nm and a beam power of 100 mW. All data was collected in log mode through a Cicero™ Interface and CyCLOPS version 3.13 data acquisition software (Cytomation, Inc., Fort Collins, Colo.). A 530 nm longpass filter (Corning Glass Works), was used to collect fluorescence intensity data from PHB stained with nile red. Increased cellular fluorescence corresponds to increased levels of PHA. The flow cytometer acquires light scatter and fluorescence signal data from stained single cells at about 20,000 cells per sample. The mean of this large cell population is shifted to higher values on the fluorescence scale when the polymer is present in greater amounts.

Screening of the DNA-shuffled mutants: gas chromatography. A hydrochloric acid propanolysis method was utilized for gas chromatographic quantification of PHB (V. Riis et al., *J. Chromatogr.*, 445, 285–289 (1988), incorporated herein by reference, in its entirety). Baffled 250 ml shake flasks containing 2× YT+1% (w/v) glucose were harvested at OD$_{436}$=4.0 and assayed for PHB content. The detailed protocols used have been described previously (J. J. Hahn et al., *Biotechnol. Prog.*, 13, 347–354 (1997), incorporated herein by reference, in its entirety).

Bioreactor experiments. DH5α/pPT700 (unshuffled) and DH5α harboring a mutant plasmid (the result of DNA shuffling) were grown using two 2 liter bioreactors (LH Fermentation, Hayward, Calif., Model 502D) running simultaneously. These bioreactors contained 2× YT+1% (w/v) glucose medium and freshly mixed kanamycin was at 100 μg ml$^{-1}$. Standard bioreactor parameters were 1 vvm (volume of air per volume of reactor content per minute) aeration, 700 rpm agitation, 30° C. temperature, and pH 7.0. Dissolved oxygen was monitored but not controlled. The pH was monitored, and controlled using a base solution of 1 M NaOH and an acid solution of 4% (v/v) phosphoric acid.

Results and discussion. The background of enzymes present on pPT700, which includes β-ketothiolase (phbA) and NADPH-dependent acetoacetyl-CoA reductase (phbB), produces 3-hydroxybutyryl-CoA monomers suitable for incorporation into PHB. The positive control pPT500 contains the native *R. eutropha* PHB synthase gene (phbC) as well as these background enzymes, and therefore represents the full PHB biosynthesis operon from *R. eutropha*. pPT500 is able to produce PHB up to approximately 60% of cell dry weight in *E. coli* grown in LB medium with 1% (w/v) glucose and 100 μg ml$^{-1}$ kanamycin. The negative control, in the form of pPT700 where phbC from *R. eutropha* has been replaced by the native *P. oleovorans* polymerase I gene, phaC1, is able to support accumulation of PHB to only 0.3% of cell dry weight under the same conditions, as measured in this laboratory (refer to FIG. 8, described in detail below), and as reported by Qun et al. ("Substrate specificity of poly-3-hydroxyalkanoate polymerases from *Pseudomonas oleovorans* GPo1", presented in a poster at the meeting of the International Symposium on Bacterial Polyhydroxyalkanoates 1996, Davos, Switzerland, 18–23 Auguest 1996). The assay, then, for successful extension of the substrate specificity in phaC1 as a result of genetic mutation involves determining whether the production of PHB in the transformed *E. coli* rises above the background level of approximately 0.3% cell dry weight. An increase in PHB production over the background level in the transformed cells containing the shuffled phaC1 on pPT700 should indicate the specificity of the enzyme has been altered toward incorporation of higher ratios of short chain length (SCL) monomers.

Fluorescence spectroscopy was used to compare the appearances of DH5α/pPT500 (the positive control for production of PHB) and DH5α/pPT700 (the negative control for production of PHB) after growth on media known to enhance PHB production (i.e., media that contained 1–2% wt/vol glucose). The comparison was made after staining the cells with nile red to highlight PHB accumulation. Each strain had been grown 48 hours on 2× YT+1% (wt/vol) glucose plates. It was evident that DH5α/pPT500 cells, where the full PHB biosynthesis operon is present, accumulated a much higher quantity of PHB. When the two strains were mixed together intentionally and grown 48 hours on a similar plate, a significant difference in colony opacity between the two types of cells was readily apparent to visual inspection.

Figure 5:
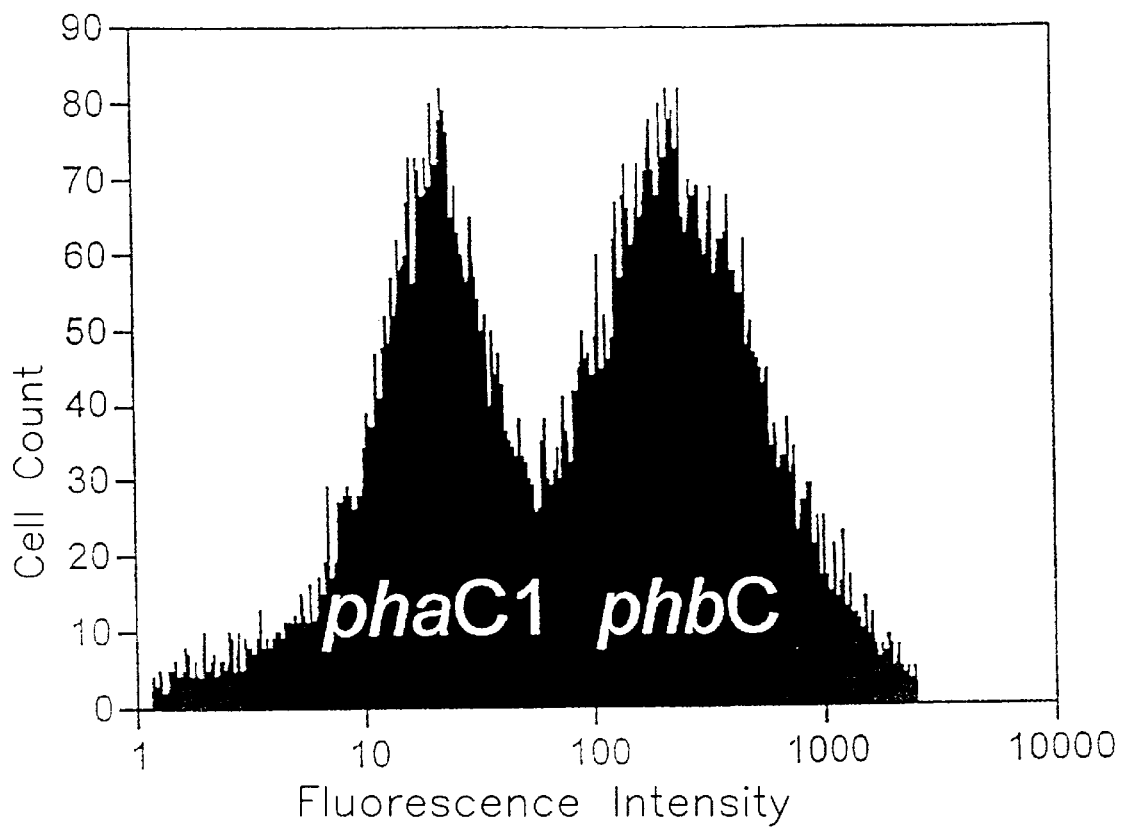
FIG. 5. Flow cytometer histogram of a mixture of DH5α harboring pPT500 and DH5α harboring pPT700.

FIG. 5 shows a flow cytometry histogram acquired from the mixture of these two stained strains. The two populations were easily resolved, and the population means were separated by approximately one order of magnitude. The flow cytometer can therefore be expected to serve as a sensitive screening tool for isolating successfully mutated phaC1 genes expressing polymerases that are able to support the synthesis of more PHB than the wild-type phaC1 gene product.

Figure 6:
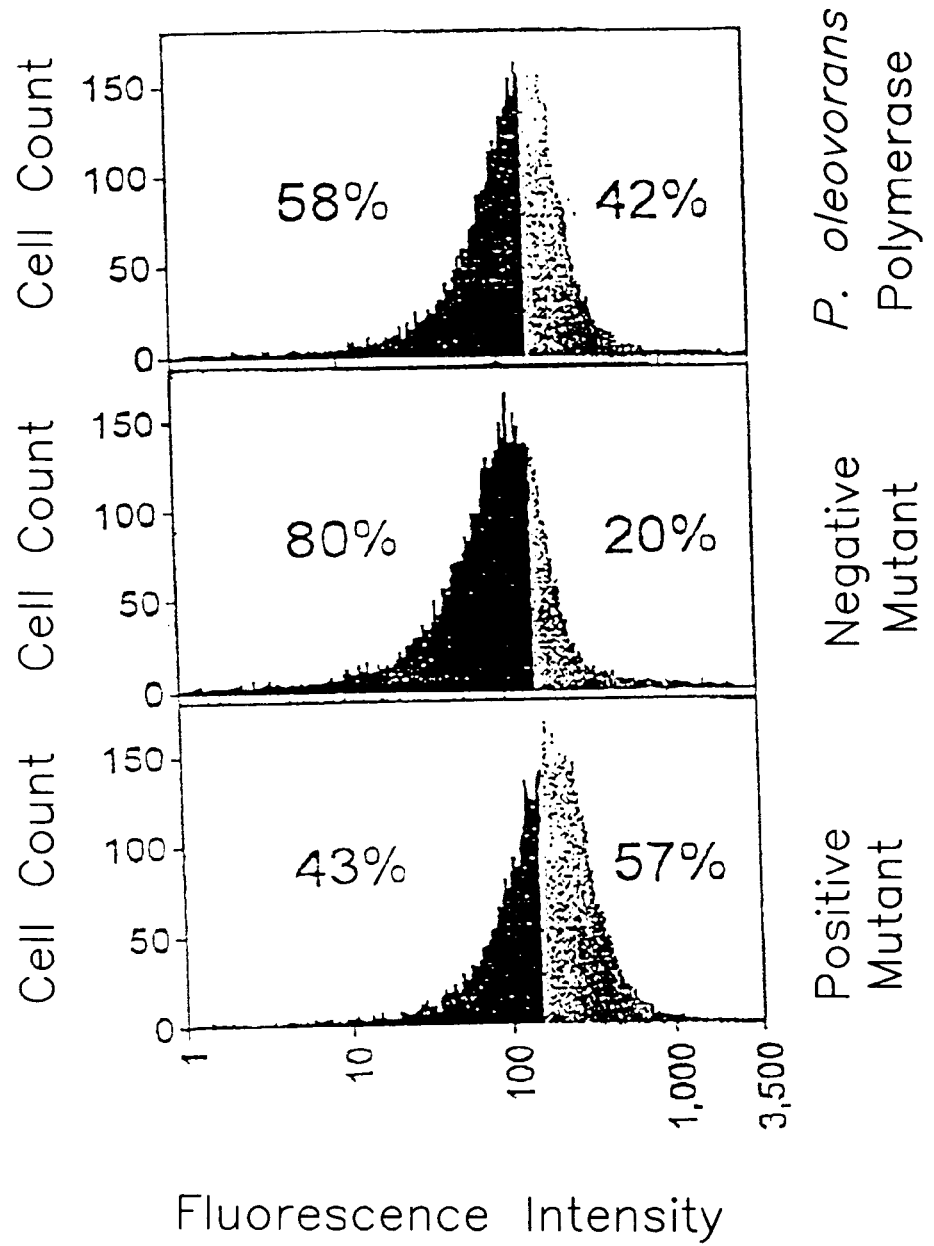
FIG. 6. Comparison of three representative sample histograms acquired using the flow cytometer. The mean from the top graph, P. oleovorans wild-type polymerase, is also represented on the other two graphs. A shift of the population to the left in the second graph, and to the right in the third graph, is easily observed and quantified.

FIG. 6 shows flow cytometer histograms acquired from three cell populations, stained identically with nile red, that exhibit significant differences in fluorescence intensity. The three cell populations include one DH5α population harboring pPT700 (negative control), and two DH5α populations harboring pPT700 containing a DNA-shuffled phaC1 gene. The mean of the top graph, which was acquired from DH5α harboring pPT700 (wild-type phaC1, the negative control), is represented on all three graphs by a difference in shading. The bottom two graphs show cells that are expressing pPT700 with phaC1 that has presumably been mutated. In the middle graph, the population has clearly shifted to the left, indicative of decreased fluorescence intensity. This suggests a mutation which has decreased the PHB productivity of phaC1. In the bottom graph, the population has shifted to the right, indicative of fluorescence intensity. This shift suggests a mutation that has, desirably, increased the PHB productivity of phaC1, representing an extension of substrate specificity in this first round mutant. The percentages on the graph represent percentages of total cell count above and below the wild type mean.

Figure 7:
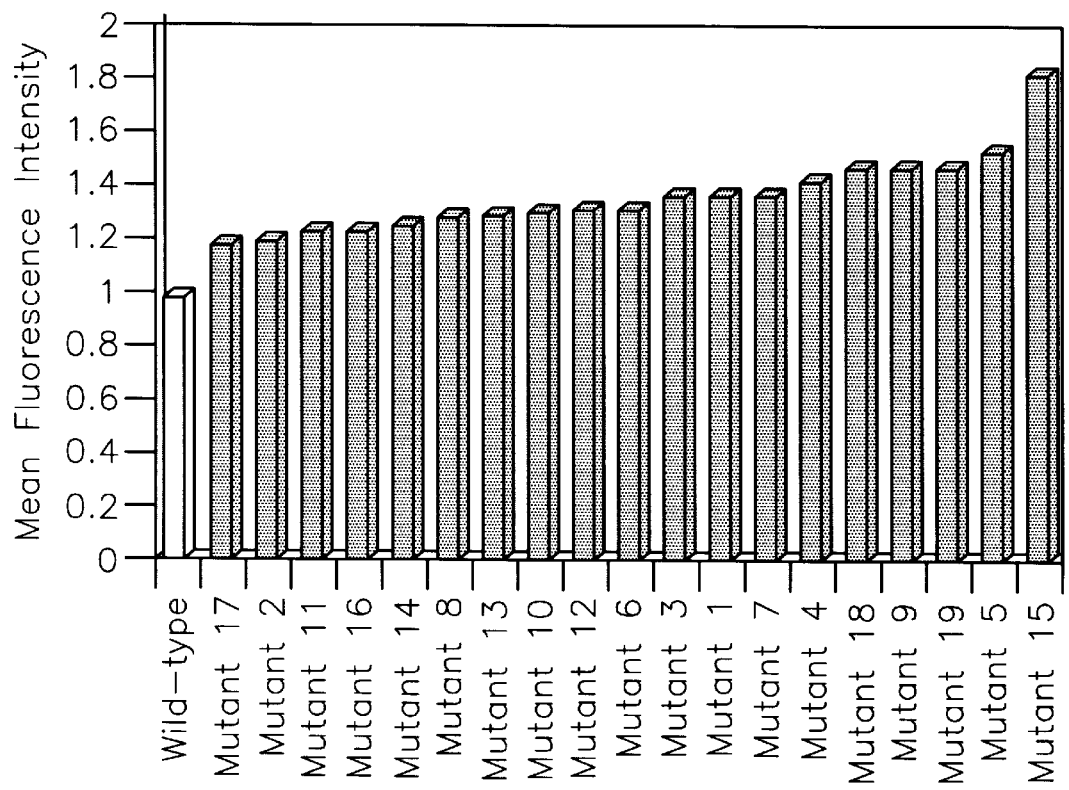
FIG. 7. Mean fluorescence intensity (MFI) of mutants expressing precursor-forming genes of R. eutropha and the P. oleovorans polymerase I on pPT700, normalized to wild-type.

This first round of shuffling was performed by using the entire plasmid as a starting material. The DNA from the highest PHB producers from this first round served as the basis for five additional rounds of shuffling on the phaC1 gene after removal from the plasmid in a ClaI/EcoRI restriction digest. None of these rounds yielded appreciable gains. Two additional rounds were then performed upon the first round material, once using the whole plasmid and once using the gene as isolated by restriction digest. FIG. 7 shows a collection of mutant genes from the first round (mutants 1–13) and from the final two rounds (mutants 14–190 that produce PHB in excess of wild-type. Mutants in phaC1 accumulating at least 20% additional PHB above wild-type phaC1 levels are shown. This assessment is based on flow cytometry determinations of mean fluorescence intensity after staining with nile red. FIG. 7 represents data averaged over several trials, including trials in which the plasmids were transformed into fresh competent DH5α as a control for any unintended host cell effects. A "trial" is a separate transformation for the same plasmid DNA into DH5α cells, which were then grown and stained identically to other "trials." Mutants that were isolated during DNA shuffling and shown in FIG. 7 are specifically identified in a table (FIG. 8). The letter P designates a round where the entire plasmid was digested with DNase I, and G represents a round where the phaC1 gene was removed with a restriction digest and then digested with DNase I. The number immediately following the initial letter represents the round number, and the number following the hyphen represents an isolate from that round. The rounds were performed in this order: P1, G2, G3, G4, G5, G6, G7, P2.

Figure 9:
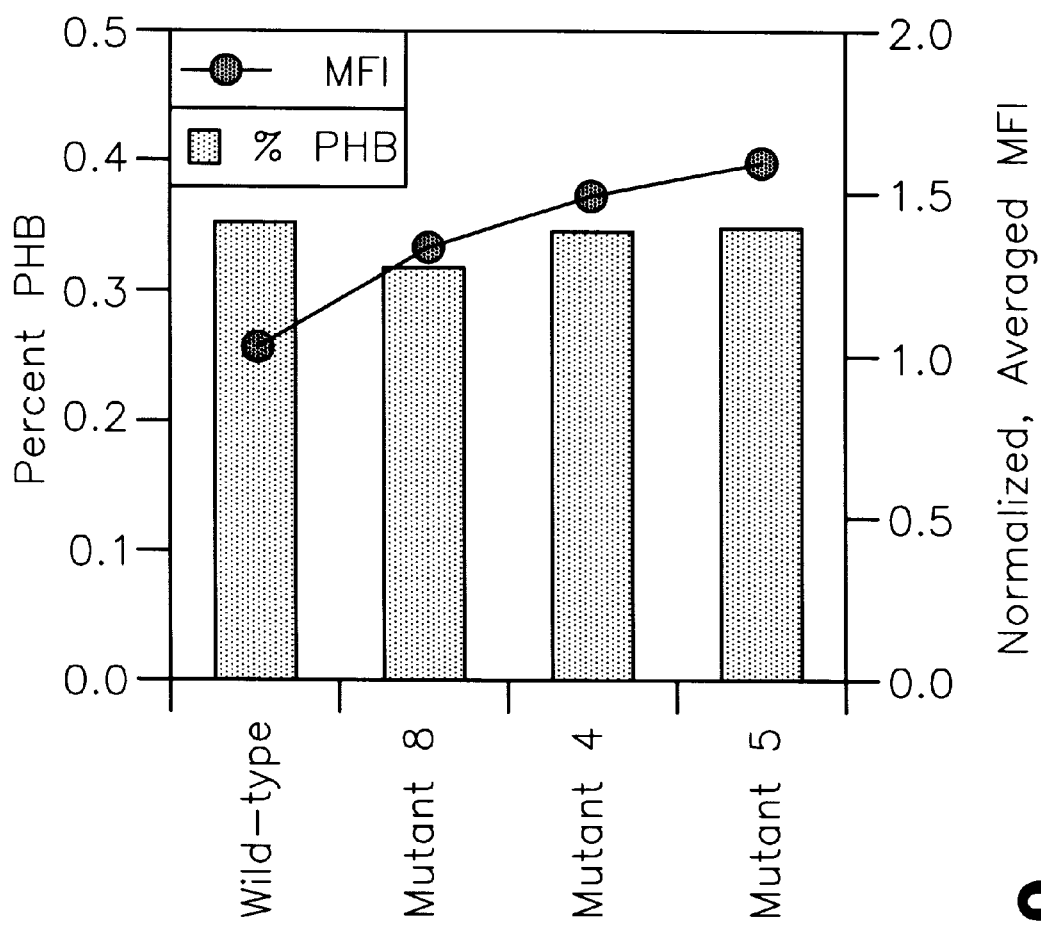
FIG. 9. PHB content of potential positive mutants. Also shown is the averaged and normalized flow cytometer results presented in FIG. 7.

FIG. 9 shows the results of gas chromatography analysis of some of the potential positive mutants from round 1. MFI is mean fluorescence intensity, as shown in FIG. 7. In this experiment, it seemed that there had been no increase over baseline levels for the negative control in PHB production achieved. No intracellular granules could be observed in these cultures using nile red staining and the fluorescence microscope, although such granules could be observed in cells from a plate culture. On this basis, and on the basis of repeated flow cytometer analysis, it was determined to carry out a comparative bioreactor experiment with one potential positive strain (mutant 5) and a control, to examine the time course of PHB accumulation.

Figure 10:
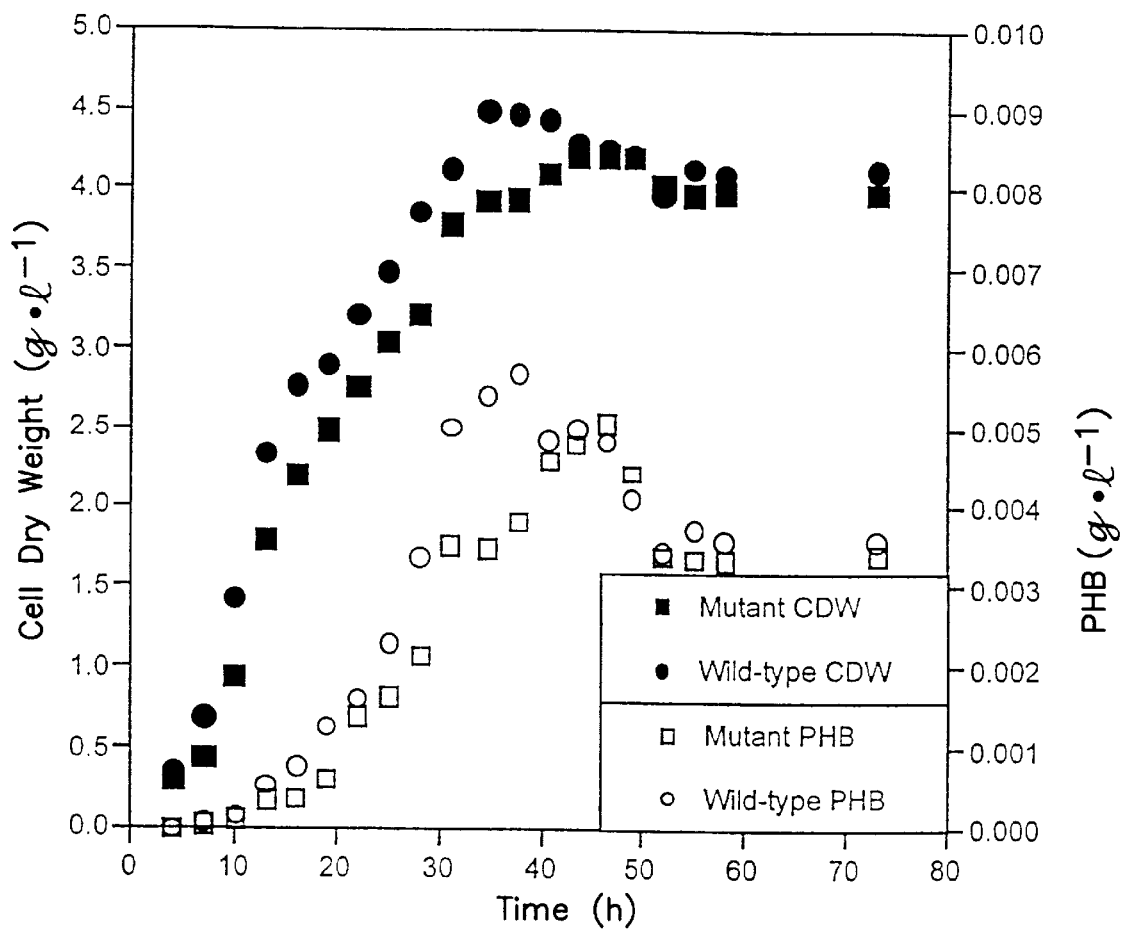
FIG. 10. DH5α/mutant and DH5α/pPT700 bioreactor cultivation. CDW=cell dry weight.

Bioreactor cultivation was performed with DH5α/pPT700, which contains the wild type phaC1 (the negative control), and mutant 5 from the first round. Here it may be observed that the DH5α culture went through diauxic growth, at first utilizing the carbon and energy sources available in 2× YT medium, and later growing on organic acid products from the first growth phase. Although large granules could be observed in the cells, the highest PHB level recorded is 0.13%. This amount of PHB appears to be less than the amount shown in FIG. 10, and this may be due to a failure to lyse the E. Coli cells during the propanolysis procedure. Presumably, granules failed to accumulate in the prior experiment due to oxygen limitation in the shake flasks. The decrease in PHB levels observed after 40 hours is not explained, since E. coli probably does not have the enzymes necessary to break down PHB.

Of the negative colonies isolated during the screening process, most did not contain mutated phaC1, but instead were products of recombination events during ligation. However, 12 true mutants were found. Since approximately 10,000 colonies were screened during this study, this gives a rate of approximately 12/10,000 or a 0.1% chance of mutations very detrimental to polymerization of 3-hydroxybutyrate into PHB by phaC1 occurring. Many more plasmids had minor errors which resulted in smaller decreases in PHB production. Such changes, although invisible to the eye, were easily found during flow cytometer screening among mutants selected as the having the whitest appearance during a particular round. This is particularly true of the five rounds that yielded no mutants able to incorporate PHB at levels higher than wild-type. In these rounds, apparently all mutations were negative ones.

DNase I will alter its specificity depending on which divalent cation is included in the reaction mixture. When $Mg^{2+}$ is included, the enzyme produces nicks in duplex DNA. When $Mn^{2+}$ is included, on the other hand, the enzyme produces double-stranded breaks in DNA (S. Tabor, "Deoxyribonuclease I (DNase I)" in: Ausubel, F. M et al., Eds., Current Protocols in Molecular Biology, John Wiley & Sons, Inc., Sections 3.13.1–3.13.2 (1989)). When an increased number of errors is desired, presumably $Mg^{2+}$ is to be preferred. Indeed, a high percentage of these nicks will be hidden until the first melting step of PCR, when many of the fragments will become too short to serve as primers (I. A. J. Lorimer et al., Nuc. Acids Res., 23, 3067–3068 (1995)). The manufacturer's conditions (Stratagene, Inc., La Jolla, Calif.), which were followed, were 40 mM Tris-HCl (pH 7.5), 6 mM $MgCl_2$ and 2 mM $CaCl_2$. Since $Ca^{2+}$ is, like $Mg^{2+}$, a divalent cation, it may have had unexpected effects on the reaction. It is possible that optimum conditions for errors were not achieved. In addition, more mutants with extended substrate specificity may result from shuffling the whole plasmid instead of just the gene itself. Zhao et al. (Nuc. Acids. Res. 25, 1307–1308 (1997)) found that isolation of a gene using a restriction enzyme digest prior to shuffling increases the fidelity of the recombination process; in contrast, it would have been preferable in this experiment to decrease the fidelity of recombination.

EXAMPLE II

Extension of Substrate Specificity of Ralstonia eutropha phbC Polyhydroxybutyrate (PHB) Polymerase Normally E. coli does not support $PHA_{MCL}$ synthesis from "Class II" PHA polymerases (i.e., $PHA_{MCL}$ polymerases) because it does not produce the necessary precursors in sufficient amounts. However, DiRusso has constructed an E. coli fadB mutant (strain LS1298) which, when transformed with a gene encoding when a Class II polymerase from Pseudomonas aeruginosa, is able to accumulate significant amounts of PHA$_{MCL}$ (C. C. DiRusso, J. Bacteriol., 172, 6459–6468 (1990), incorporated herein by reference in its entirety). E. coli LS1298 was formed by creating a chromosomal insertion of a kanamycin resistance coding sequence. During growth of the transformed host on LB medium containing 0.5% (w/v) decanoic acid, polymer was accumulated at 21% of cell dry weight in the form of a copolymer that contained mostly 3-hydroxydecanoate (72.5 mol %) together with other medium chain length PHA (S. Langenbach et al., FEMS Microbiol. Lett., 150, 303–309 (1997). This E. coli fadB mutant (strain LS1298) was obtained from Concetta DiRusso it (C. C. DiRusso, J. Bacteriol., 172, 6459–6468 (1990)), and can be used to screen shuffled polymerases for PHA$_{MCL}$ activity and hence, to detect a shift from PHA$_{SCL}$ (Class I) to PHA$_{MCL}$ (Class II) specificity.

Figure 2:
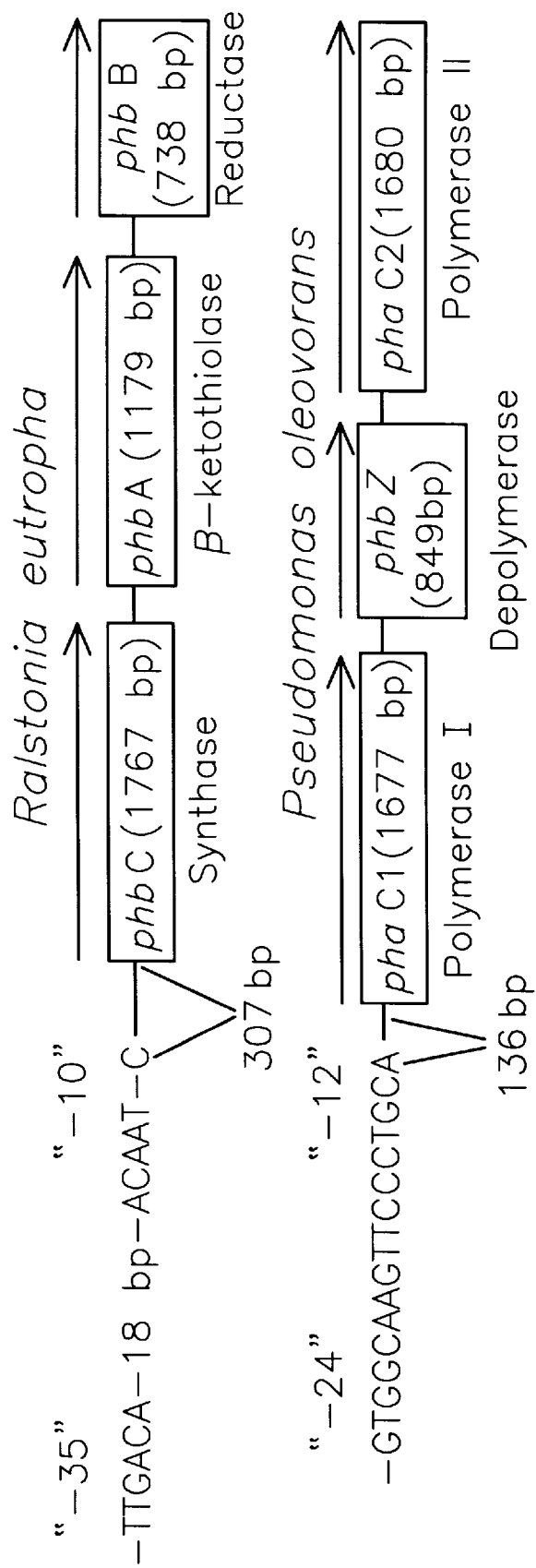
FIG. 2. Organization of the PHA gene operons in R. eutropha and P. oleovorans.

A modified version of the plasmid pPT500 (see Example I) is used as the DNA shuffling vector. As described in Example I, pPT500 contains the full Ralstonia eutropha PHB biosynthesis operon, including promoter (see FIG. 2). Prior to DNA shuffling of the PHB polymerase, the ketothiolase and reductase coding regions are deleted to render the biosynthetic pathway for PHB inactive in the E. coli host; it has been shown that PHB polymerase from Ralstonia eutropha does not produce PHB in E. coli in the absence of the other two enzymes of the PHB operon, β-ketothiolase and acetoacetyl-CoA reductase. The plasmid pPT500 possesses both kanamycin and zeocin resistance; thus zeocin is used for selection since the E. coli host is already kanamycin resistant. Alternatively, the gene encoding the PHB polymerase (or any other desired Class I polymerase) can be freshly cloned into a pUC-based vector, permitting selection of the plasmid with ampicillin.

After DNA shuffling of this polymerase and expression of the mutated genes in E. coli LS1298, accumulation of polymer under the described growth conditions is evidence that the specificity of a Class I polymerase has been extended to include a Class II polymerase activity. The formation of PHA can be recognized by the opaque appearance of colonies.

An alternative selection process involves exposing the transformed cells a substrate concentration (3-hydroxydecanoate) so high that it is lethal to cells that are unable to convert the substrate into the polymer.

EXAMPLE III
DNA Shuffling and Selection for Polymerase Exhibiting Extended Substrate Specificity from an Initial Mixture of PHA$_{SCL}$ and PHA$_{MCL}$ Polymerase Genes Class I and Class II polymerases show a high degree of homology. To exchange domains of the enzymes for obtaining mixed functionality, the shuffling procedure (described in Example I) can be carried out starting with a mixture of genes, at least one of which encodes a Class I polymerase and at least one of which encodes a Class II polymerase. The DNA shuffling can be carried out using DNA fragments that include the polymerase gene, or using a plasmid, such as the one described in the following paragraph, into which the genes have been cloned.

After DNA shuffling is complete, the shuffled gene can be cloned into (or, alternatively, is already a part of) a single vector which can be used as a two-fold screen for the presence of both Class I and Class II activities in a single PHA polymerase. This vector comprises the ketothiolase and reductase genes from R. eutropha under the control of an inducible promoter, and in the shuffled PHA polymerase gene under the control of its own, separate constitutive promoter.

To screen for PHA$_{SCL}$ activity, the ketothiolase and reductase are induced to activate the required complementation pathway. Presence of PHA$_{SCL}$, detected as in Example I on LB supplemented with glucose, indicates functional PHA$_{SCL}$ activity.

When PHA$_{MCL}$ activity is being assayed, the inducible promoter is left "turned off," and the ketothiolase and reductase genes remain unexpressed. Production of PHA$_{MCL}$ is detected using the assay set forth in Example II, by transforming the E. coli fadB mutant (strain LS1298) and supplying the proper substrate (decanoic acid).

A vector that is able to support production of PHA both in both assays contains a bispecific PHA polymerase, i.e., a PHA polymerase having both PHA$_{SCL}$ and PHA$_{MCL}$ activities. Additionally or alternatively, it may be possible to select for mutants that can accumulate higher amounts of polymer by increasing glucose or decanoic acid to near-toxic levels, where a strain that does not produce sufficient polymer cannot survive.

EXAMPLE IV

Gene Shuffling and Isolation of Other Catalytic Activities Involved in PHA Synthesis Because E. coli DH5α is unable to synthesize PHB even in the presence of PHB polymerase, this system can be used to isolate and modify enzyme activities, such as β-ketothiolase or acetoacetyl-CoA reductase activity, that catalyze precursor formation for PHB. The presence of these enzymatic activities can be detected by the formation of PHB in a strain that has been transformed with the PHB polymerase gene. For example, this system can be used to screen for a multifunctional enzyme complex comprising both reductase activity and polymerase activity, for example a single gene encoding a bifunctional protein, which gene is the product of a fusion of genes encoding β-ketothiolase and a acetoacetyl-CoA reductase. Such enzyme will have significant kinetic advantages in PHA synthesis.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for making a nucleic acid encoding a non-naturally occurring bispecific polyhydroxyalkanoate (PHA) polymerase which polymerizes a first carbon substrate and a second carbon substrate comprising:

providing a *Pseudomonas oleovorans* phaC1 nucleic acid encoding a PHA polymerase which polymerizes the first carbon substrate; and altering the nucleic acid to yield a modified phaC1 nucleic acid encoding a non-naturally occurring bispecific PHA polymerase which copolymerizes the first carbon substrate and the second.

2. The method of claim 1 wherein the first carbon substrate is a C6–C14 monomer and the second carbon substrate is a C3–C5 monomer.

3. A modified *P. oleovorans* phaC1 nucleic acid encoding a non-naturally occurring bispecific PHA polymerase.

4. A vector comprising an inducible promoter operably linked to each of a nucleotide sequence encoding a β-ketothiolase and a nucleotide sequence encoding an acetoacetyl-CoA reductase, and a constitutive promoter operably linked to a modified *P. oleovorans* phaC1 nucleic acid encoding a non-naturally occurring bispecific PHA polymerase.

5. A vector comprising a promoter operably linked to a modified *P. oleovorans* phaC1 nucleic acid encoding a non-naturally occurring bispecific PHA polymerase.

6. A method for making a non-naturally occurring bispecific PHA polymerase comprising:

providing a modified *P. oleovorans* phaC1 nucleic acid encoding a non-naturally occurring bispecific PHA polymerase which copolymerizes a first carbon substrate and a second carbon substrate; and transforming a bacterial, yeast or plant host cell with the nucleic acid to yield a transformed host cell that produces the non-naturally occurring bispecific PHA polymerase.

7. The method of claim 6 wherein the first carbon substrate is a C3–C5 monomer and the second carbon substrate is a C6–C14 monomer.

8. The method of claim 6 wherein the step of providing a modified *P. oleovorans* phaC1 nucleic acid comprises:

providing a *P. oleovorans* phaC1 nucleic acid encoding a PHA polymerase which copolymerizes the first carbon substrate; and altering the nucleic acid encoding the PHA polymerase to yield a modified *P. oleovorans* phaC1 nucleic acid encoding the non-naturally occurring bispecific PHA polymerase which copolymerizes the first carbon substrate and the second carbon substrate.

9. The method of claim 8 wherein the first carbon substrate is a C6–C14 monomer and the second carbon substrate is a C3–C5 monomer.

10. A method for making a polyhydroxyalkanoate (PHA) copolymer comprising:
   (a) transforming a bacterial, yeast or plant host cell with a modified *P. oleovorans* phaC1 nucleic acid encoding a non-naturally occurring bispecific PHA polymerase to yield a transformed host cell that produces the non-naturally occurring bispecific PHA polymerase, resulting in the production of a PHA copolymer comprising at least one C3–C5 monomer and at least one C6–C14 monomer; and
   (b) isolating the PHA copolymer from the bacterial, yeast or plant host cell.

11. The method of claim 10 wherein the nucleic acid is in a vector, wherein the vector comprises a promoter operably linked to the nucleic acid.

12. The method of claim 11 wherein the vector further comprises three stop codons positioned immediately 3' to the nucleic acid, wherein the three stop codons are staggered so as to insure termination of synthesis of the PHA polymerase irrespective of reading frame.

13. The method of claim 10 further comprising, prior to or concurrent with step (a), supplying the host cell with at least one carbon substrate that can be polymerized by the non-naturally occurring bispecific PHA polymerse to form the PHA copolymer.

14. The method of claim 10 wherein the host cell is a bacterial cell.

15. The method of claim 10 wherein the host cell is a yeast cell.

16. The method of claim 10 wherein the host cell is a plant cell.

17. The method of claim 10 wherein the cell comprises a peroxisome, and wherein the non-naturally occurring bispecific PHA polymerase encoded by the nucleic acid comprises an amino acid sequence targeting the non-naturally occurring bispecific PHA polymerase to the peroxisome.

18. The method of claim 17 wherein the peroxisome is a glyoxysome.

19. A method for making a polyhydroxyalkanoate (PHA) copolymer in a transgenic plant comprising:
   (a) providing a transgenic plant comprising a modified *P. oleovorans* phaC1 nucleic acid encoding a non-naturally occurring bispecific PHA polymerase, wherein the transgenic plant produces the non-naturally occurring bispecific PHA polymerase resulting in production of a PHA copolymer comprising at least one C3–C5 monomer and at least one C6–C14 monomer; and
   (b) isolating the PHA copolymer from the plant.

20. The method of claim 19 wherein step (b) comprises isolating the PHA copolymer from the seed of the plant.

21. The method of claim 19 wherein the non-naturally occurring bispecific PHA polymerase encoded by the nucleic acid comprises an amino acid sequence targeting the non-naturally occurring bispecific PHA polymerase to a plant cell peroxisome.

22. The method of claim 21 wherein the peroxisome is a glyoxysome.

23. A transgenic organism comprising a modified *P. oleovorans* phaC1 nucleic acid encoding a non-naturally occurring bispecific PHA polymerase, wherein the transgenic organism is selected from the group consisting of a bacterium, a yeast and a plant.

24. The transgenic organism of claim 23 that is a plant.

* * * * *

UNITED STATES PATENT AND TRADEMARK OFFICE
CERTIFICATE OF CORRECTION

PATENT NO.   : 6,143,952
DATED        : November 7, 2000
INVENTOR(S)  : Srienc et al.

It is certified that error appears in the above-identified patent and that said Letters Patent is hereby corrected as shown below:

Claim 1,
Line 11, after "second" insert -- carbon substrate --.

Signed and Sealed this

Sixth Day of November, 2001

Attest:

*Attesting Officer*

NICHOLAS P. GODICI
*Acting Director of the United States Patent and Trademark Office*

SEQUENCE LISTING

<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 1
gggagatctc ccgggaagt accttgccga                                  30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
aggatcgatt gattgtctct ctgccgtcac                                  30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 3
attatcgatg gcgaccggca aaggcgcggc                                  30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 4
gccgaattca tgccttggct ttgacgtatc                                  30

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 5
cacgaattct gagtgaacgc ttgcatgagt gccggcgtg                        39

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6
atactcgagc cgcgagggcc gcgctgcacg                                  30

<210> SEQ ID NO 7
<211> LENGTH: 31

```
<212> TYPE: DNA
<213> ORGANISM: Artificial Sequence
<220> FEATURE:
<223> OTHER INFORMATION: Description of Artificial Sequence: Primer

<400> SEQUENCE: 7
attatcgatg agtaacaaga acaacgatga g                               31

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 8
ggaattcaac gctcgtgaac gtaggt                                     26

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 9
tatcggaatg gacgcaag                                              18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 10
catgatgact tcgctcacc                                             19
```